US012589243B2

(12) United States Patent
Chiapetta et al.

(10) Patent No.: US 12,589,243 B2
(45) Date of Patent: Mar. 31, 2026

(54) OCULAR DEVICES AND CONTROLLER INTERFACES FOR OCULAR THERAPY

(71) Applicant: i-Lumen Scientific, Inc., Bloomington, MN (US)

(72) Inventors: James R. Chiapetta, Delano, MN (US); Paul Rockley, Corona Del Mar, CA (US); Ronald Schuchard, Wichita, KS (US)

(73) Assignee: i-Lumen Scientific, Inc., Bloomington, MN (US)

( * ) Notice: Subject to any disclaimer, the term of this patent is extended or adjusted under 35 U.S.C. 154(b) by 273 days.

(21) Appl. No.: 18/491,385

(22) Filed: Oct. 20, 2023

(65) Prior Publication Data

US 2024/0131334 A1 Apr. 25, 2024
US 2024/0226555 A9 Jul. 11, 2024

Related U.S. Application Data

(60) Provisional application No. 63/418,375, filed on Oct. 21, 2022.

(51) Int. Cl.
*A61N 1/36* (2006.01)
*A61N 1/04* (2006.01)

(52) U.S. Cl.
CPC ....... *A61N 1/36046* (2013.01); *A61N 1/0472* (2013.01)

(58) Field of Classification Search
CPC .......................... A61N 1/36046; A61N 1/0472
See application file for complete search history.

(56) References Cited

U.S. PATENT DOCUMENTS

| | | | |
|---|---|---|---|
| 2,283,752 A | 5/1942 | Gonsett | |
| 2,527,947 A | 10/1950 | Loos | |
| 2,760,483 A | 8/1956 | Tassicker | |
| 3,376,870 A | 4/1968 | Yamamoto et al. | |
| 3,669,119 A | 6/1972 | Symmes | |
| D246,529 S | 11/1977 | Willard | |
| 4,162,542 A | 7/1979 | Frank | |
| D280,670 S | 9/1985 | Fireman | |
| 4,551,149 A | 11/1985 | Scairra | |
| 4,614,193 A | 9/1986 | Liss et al. | |

(Continued)

FOREIGN PATENT DOCUMENTS

| | | |
|---|---|---|
| CN | 1096460 A | 12/1994 |
| DE | 202012003100 U1 | 10/2012 |

(Continued)

OTHER PUBLICATIONS

Chlaihawi et al; "Development of Printed and Flexible Dry ECG Electrodes", Sensing and Bio-Sensing Research, vol. 20, pp. 9-15, 2018.

(Continued)

*Primary Examiner* — Eugene T Wu
(74) *Attorney, Agent, or Firm* — Fox Rothschild LLP

(57) ABSTRACT

Illustrative methods and devices for providing stimulus to the eye to treat vision disorders. Systems and methods for testing thresholds and configuring the stimulation for a patient are provided. Various examples may include therapies for vision disorders that can progress to blindness, such as macular degeneration or other diseases and disease processes.

9 Claims, 20 Drawing Sheets

(56)  References Cited

U.S. PATENT DOCUMENTS

| | | | |
|---|---|---|---|
| 4,628,933 A | 12/1986 | Michelson |
| 4,664,117 A | 5/1987 | Beck |
| 4,712,558 A | 12/1987 | Kidd et al. |
| 4,979,811 A | 12/1990 | Boyer |
| 5,024,223 A | 6/1991 | Chow |
| 5,109,844 A | 5/1992 | De Juan et al. |
| 5,147,284 A | 9/1992 | Fedorov et al. |
| 5,154,174 A | 10/1992 | Hawlina |
| 5,193,540 A | 3/1993 | Schulman et al. |
| 5,263,200 A | 11/1993 | Miller |
| 5,522,864 A | 6/1996 | Wallace et al. |
| 5,556,423 A | 9/1996 | Chow et al. |
| 5,597,381 A | 1/1997 | Rizzo, III |
| 5,643,330 A | 7/1997 | Holsheimer et al. |
| 5,836,996 A | 11/1998 | Doorish |
| 5,843,147 A | 12/1998 | Testerman et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 6,007,532 A | 12/1999 | Netherly |
| D421,124 S | 2/2000 | Yavitz |
| 6,035,236 A | 3/2000 | Jarding et al. |
| D425,623 S | 5/2000 | Funk |
| D429,817 S | 8/2000 | Banks |
| 6,101,411 A | 8/2000 | Newsome |
| 6,131,208 A | 10/2000 | Banks |
| 6,154,671 A | 11/2000 | Parel et al. |
| D440,660 S | 4/2001 | Sternberg |
| 6,230,057 B1 | 5/2001 | Chow et al. |
| D444,561 S | 7/2001 | Stein |
| 6,275,735 B1 | 8/2001 | Jarding et al. |
| 6,282,449 B1 | 8/2001 | Kamerling et al. |
| 6,306,075 B1 | 10/2001 | Shadduck |
| 6,324,429 B1 | 11/2001 | Shire et al. |
| 6,389,317 B1 | 5/2002 | Chow et al. |
| 6,400,989 B1 | 6/2002 | Eckmiller |
| 6,408,211 B1 | 6/2002 | Powell |
| 6,424,864 B1 | 7/2002 | Matsuura |
| 6,442,431 B1 | 8/2002 | Veraart et al. |
| 6,458,157 B1 | 10/2002 | Suaning |
| 6,515,227 B1 | 2/2003 | Massey et al. |
| 6,611,716 B2 | 8/2003 | Chow et al. |
| 6,755,530 B1 | 6/2004 | Loftus et al. |
| 6,792,314 B2 | 9/2004 | Byers et al. |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,031,776 B2 | 4/2006 | Chow et al. |
| 7,037,943 B2 | 5/2006 | Peyman |
| 7,043,308 B2 | 5/2006 | Cohen |
| 7,047,080 B2 | 5/2006 | Palanker et al. |
| 7,058,455 B2 | 6/2006 | Huie, Jr. et al. |
| 7,067,327 B2 | 6/2006 | Wu et al. |
| 7,130,693 B1 | 10/2006 | Montalbo |
| 7,139,612 B2 | 11/2006 | Chow et al. |
| 7,146,209 B2 | 12/2006 | Gross et al. |
| 7,147,865 B2 | 12/2006 | Fishman et al. |
| 7,158,834 B2 | 1/2007 | Paul, Jr. |
| 7,158,836 B2 | 1/2007 | Suzuki |
| 7,248,928 B2 | 7/2007 | Yagi |
| 7,251,528 B2 | 7/2007 | Harold |
| 7,306,621 B1 | 12/2007 | Halla et al. |
| 7,321,796 B2 | 1/2008 | Fink et al. |
| 7,337,008 B2 | 2/2008 | Terasawa et al. |
| 7,398,124 B2 | 7/2008 | Fujikado et al. |
| 7,400,021 B2 | 7/2008 | Wu et al. |
| 7,447,547 B2 | 11/2008 | Palanker |
| 7,447,548 B2 | 11/2008 | Eckmiller |
| 7,458,456 B2 | 12/2008 | Hogan et al. |
| 7,556,621 B2 | 7/2009 | Palanker et al. |
| 7,877,148 B2 | 1/2011 | Chowdhury et al. |
| 7,883,535 B2 | 2/2011 | Cantin et al. |
| 7,974,699 B2 | 7/2011 | Tano et al. |
| 7,979,134 B2 | 7/2011 | Chow et al. |
| 7,981,062 B2 | 7/2011 | Chow et al. |
| 8,000,804 B1 | 8/2011 | Wessendorf et al. |
| 8,039,445 B2 | 10/2011 | Behar-Cohen et al. |
| 8,070,688 B2 | 12/2011 | Livne et al. |
| 8,190,266 B2 | 5/2012 | Ameri et al. |
| 8,197,539 B2 | 6/2012 | Nasiatka et al. |
| 8,260,428 B2 | 9/2012 | Fink et al. |
| 8,265,764 B2 | 9/2012 | Tano et al. |
| 8,306,626 B2 | 11/2012 | Chow et al. |
| 8,377,120 B2 | 2/2013 | Lipshitz et al. |
| 8,396,561 B2 | 3/2013 | Pezaris et al. |
| 8,396,562 B2 | 3/2013 | Ameri et al. |
| 8,398,692 B2 | 3/2013 | Deisseroth et al. |
| 8,433,417 B2 | 4/2013 | Flood |
| 8,478,415 B1 | 7/2013 | Halla et al. |
| 8,515,548 B2 | 8/2013 | Rofougaran et al. |
| 8,612,002 B2 | 12/2013 | Faltys et al. |
| 8,634,923 B2 | 1/2014 | Sharpee et al. |
| 8,639,345 B2 | 1/2014 | Eipper et al. |
| 8,691,877 B2 | 4/2014 | Yun et al. |
| 8,700,167 B2 | 4/2014 | Sabel |
| 8,725,266 B2 | 5/2014 | Olson et al. |
| 8,731,683 B2 | 5/2014 | Lindenthaler |
| 8,734,513 B2 | 5/2014 | Wu et al. |
| 8,771,349 B2 | 7/2014 | Schachar |
| 8,788,041 B2 | 7/2014 | Yun et al. |
| 8,801,942 B2 | 8/2014 | Scorsone et al. |
| 8,824,156 B2 | 9/2014 | Tai et al. |
| 8,852,290 B2 | 10/2014 | Rowley et al. |
| 8,864,805 B2 | 10/2014 | Deisseroth et al. |
| 8,868,202 B2 | 10/2014 | Della Santina et al. |
| 8,903,495 B2 | 12/2014 | Greenberg et al. |
| 8,909,340 B2 | 12/2014 | Yun |
| 8,918,186 B2 | 12/2014 | Tiedtke |
| 8,918,188 B2 | 12/2014 | Tiedtke |
| 8,972,004 B2 | 3/2015 | Simon et al. |
| 9,002,463 B2 | 4/2015 | Tiedtke |
| 9,037,251 B2 | 5/2015 | Narayan et al. |
| 9,037,252 B2 | 5/2015 | Tiedtke |
| 9,037,255 B2 | 5/2015 | Rocke et al. |
| 9,078,743 B2 | 7/2015 | Tai et al. |
| 9,079,042 B2 | 7/2015 | Tiedtke et al. |
| 9,125,734 B2 | 9/2015 | Keller et al. |
| 9,144,608 B2 | 9/2015 | Olson et al. |
| 9,162,060 B2 | 10/2015 | Wrobel et al. |
| 9,162,061 B2 | 10/2015 | Barnes |
| 9,180,309 B2 | 11/2015 | Nirenberg et al. |
| 9,186,523 B1 | 11/2015 | Zolli |
| 9,187,745 B2 | 11/2015 | Deisseroth et al. |
| 9,199,080 B2 | 12/2015 | Gekeler et al. |
| 9,220,634 B2 | 12/2015 | Nirenberg |
| 9,220,894 B1 | 12/2015 | Zhu |
| 9,233,026 B2 | 1/2016 | Ziemeck et al. |
| 9,233,258 B2 | 1/2016 | Simon et al. |
| 9,242,067 B2 | 1/2016 | Shore et al. |
| 9,302,103 B1 | 4/2016 | Nirenberg |
| 9,322,713 B2 | 4/2016 | Narayan et al. |
| 9,326,887 B2 | 5/2016 | Yun |
| 9,339,650 B2 | 5/2016 | Rezai et al. |
| 9,345,568 B2 | 5/2016 | Cho et al. |
| 9,370,348 B2 | 6/2016 | Tally et al. |
| 9,381,355 B2 | 7/2016 | Khraiche et al. |
| 9,403,001 B2 | 8/2016 | Simon et al. |
| 9,452,289 B2 | 9/2016 | Chichilnisky et al. |
| 9,456,836 B2 | 10/2016 | Boling et al. |
| 9,468,760 B1 | 10/2016 | Lin |
| 9,498,380 B2 | 11/2016 | Berdahl et al. |
| 9,630,013 B2 | 4/2017 | Bachinski et al. |
| 9,636,212 B2 | 5/2017 | Tiedtke et al. |
| 9,682,232 B2 | 6/2017 | Shore et al. |
| 9,687,652 B2 | 6/2017 | Franke et al. |
| 9,697,746 B2 | 7/2017 | Barnes et al. |
| 9,737,710 B2 | 8/2017 | Fan |
| 9,737,711 B2 | 8/2017 | Twyford et al. |
| 9,789,312 B2 | 10/2017 | Fukuma et al. |
| 9,795,787 B2 | 10/2017 | Cho et al. |

(56) References Cited

U.S. PATENT DOCUMENTS

| | | | |
|---|---|---|---|
| 9,821,003 | B2 | 11/2017 | Yun |
| 9,821,159 | B2 | 11/2017 | Ackermann et al. |
| 9,844,459 | B2 | 12/2017 | Badawi |
| 9,867,988 | B2 | 1/2018 | Fink et al. |
| 9,884,180 | B1 | 2/2018 | Ho et al. |
| 9,895,529 | B2 | 2/2018 | Tiedtke |
| 9,925,373 | B2 | 3/2018 | Nirenberg |
| 9,931,506 | B2 | 4/2018 | Chung et al. |
| 9,937,346 | B2 | 4/2018 | Lineaweaver et al. |
| 9,950,153 | B2 | 4/2018 | Wagner et al. |
| 9,956,425 | B2 | 5/2018 | Peyman |
| 9,962,540 | B2 | 5/2018 | Picaud et al. |
| 9,962,558 | B2 | 5/2018 | Peyman |
| 9,980,388 | B2 | 5/2018 | Tai et al. |
| 9,990,861 | B2 | 6/2018 | Chichilnisky et al. |
| 10,010,364 | B2 | 7/2018 | Harrington |
| 10,071,251 | B2 | 9/2018 | Bachinski et al. |
| 10,112,048 | B2 | 10/2018 | Franke et al. |
| 10,129,647 | B2 | 11/2018 | Seo et al. |
| 10,347,050 | B1 | 7/2019 | Wang et al. |
| 11,305,118 | B2 | 4/2022 | Rockley et al. |
| 11,338,139 | B2 | 5/2022 | Rockley et al. |
| 11,471,680 | B2 | 10/2022 | Chiapetta et al. |
| 11,511,112 | B2 | 11/2022 | Mullins et al. |
| 2003/0158588 | A1 | 8/2003 | Rizzo et al. |
| 2003/0233135 | A1 | 12/2003 | Yee |
| 2003/0233137 | A1 | 12/2003 | Paul, Jr. |
| 2004/0106965 | A1 | 6/2004 | Chow |
| 2004/0176820 | A1 | 9/2004 | Paul, Jr. |
| 2005/0004625 | A1 | 1/2005 | Chow |
| 2005/0049578 | A1 | 3/2005 | Tu et al. |
| 2005/0137649 | A1 | 6/2005 | Paul, Jr. |
| 2006/0142818 | A1 | 6/2006 | Chow et al. |
| 2007/0093877 | A1 | 4/2007 | Beecham et al. |
| 2008/0171929 | A1 | 7/2008 | Katims |
| 2008/0194531 | A1 | 8/2008 | Steer et al. |
| 2009/0217938 | A1 | 9/2009 | Rabe et al. |
| 2009/0287276 | A1 | 11/2009 | Greenberg et al. |
| 2011/0081333 | A1 | 4/2011 | Shantha et al. |
| 2012/0123501 | A1 | 5/2012 | Greenberg et al. |
| 2013/0053733 | A1 | 2/2013 | Korb et al. |
| 2013/0066396 | A1 | 3/2013 | Gekeler et al. |
| 2013/0184782 | A1 | 7/2013 | Eipper et al. |
| 2014/0257433 | A1 | 9/2014 | Ackermann et al. |
| 2014/0277435 | A1 | 9/2014 | Gefen |
| 2015/0039067 | A1 | 2/2015 | Greenberg et al. |
| 2016/0051439 | A1 | 2/2016 | Brown et al. |
| 2016/0317474 | A1 | 11/2016 | Aung et al. |
| 2017/0266445 | A1 | 9/2017 | O'Clock |
| 2018/0064935 | A1 | 3/2018 | Leonhardt et al. |
| 2018/0228237 | A1 | 8/2018 | Zhang et al. |
| 2018/0318585 | A1 | 11/2018 | Pfeifer |
| 2018/0318586 | A1 | 11/2018 | Salazar |
| 2020/0101290 | A1* | 4/2020 | Rockley ............... A61N 1/3603 |
| 2020/0171307 | A1 | 6/2020 | Rockley et al. |
| 2020/0324114 | A1 | 10/2020 | Chiapetta et al. |
| 2022/0296899 | A1 | 9/2022 | Rockley et al. |

FOREIGN PATENT DOCUMENTS

| | | | |
|---|---|---|---|
| EP | 1985332 | A1 | 10/2008 |
| GB | 2246709 | A | 12/1992 |
| WO | 2006086452 | A1 | 8/2006 |
| WO | 2013124141 | A1 | 8/2013 |
| WO | 2015095257 | A2 | 6/2015 |
| WO | 2016089751 | A1 | 6/2016 |
| WO | 2017048731 | A1 | 3/2017 |
| WO | 2017064500 | A1 | 4/2017 |
| WO | 2018013835 | A1 | 1/2018 |
| WO | 2018129351 | A1 | 7/2018 |
| WO | 2018208009 | A1 | 11/2018 |
| WO | 2020264263 | A1 | 12/2020 |
| WO | 2021011255 | A1 | 1/2021 |

OTHER PUBLICATIONS

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncorneal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC. 2023 (No Year Given).

Stauffer et al; "Skin Conformal Polymer Electrodes for Clinical ECG and EEG Recordings," Advanced Healthcare Materials pp. 1-10, 2018.

Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

Invitation To Pay Additional Fees dated Dec. 17, 2019 for International Application No. PCT/US2019/054028.

Invitation To Pay Additional Fees dated Feb. 14, 2020 for International Application No. PCT/US2019/063580.

International Search Report and Written Opinion dated Jul. 10, 2020 for International Application No. PCT/US2020/027438.

Krakova et al., "Spatial Differences in Corneal Electroretinogram Potentials Measured in Rat with a Contact Lens Electrode Array," Doc Ophthalmol vol. 129, pp. 151-166, 2014.

U.S. Appl. No. 17/782,100, filed Jun. 21, 2022.

* cited by examiner

404

OCULAR DEVICES AND CONTROLLER INTERFACES FOR OCULAR THERAPY

CROSS REFERENCE TO RELATED APPLICATIONS

The present application claims the benefit of and priority to US Provisional Patent Application 63/418,375, filed Oct. 21, 2022, titled OCULAR DEVICES AND CONTROLLER INTERFACES FOR OCULAR THERAPY, the disclosure of which is incorporated herein by reference.

FIELD

The present invention relates generally to the field of ophthalmic treatments for diseases of the eye. More particularly, the present invention is directed to systems and methods adapted to provide stimulus, such as by electrical stimuli, to the eye.

BACKGROUND

Therapy to prevent or reverse diseases of the eye is of great interest. As life expectancy expands, more and more of the population is at risk for age related macular degeneration (AMD). Meanwhile, smaller populations of young patients suffer from a variety of genetic diseases, including Stargardt's disease, that affect the retina of the eye. A wide variety of other vision disorders exist which can lead to partial or total blindness. New and alternative methods and systems for treating such diseases are desired.

OVERVIEW

There is a continuing demand for new and alternative systems and methods to treat such disorders including by preventing, arresting or reversing disease progress, or at least by alleviating ongoing symptoms.

It has generally been the case that the phosphenes are observed/used as an indicator that electric fields induced by a therapy apparatus are reaching a desired target, which may be, for example, the retina. The occurrence of phosphenes indicates an action potential or firing of one of the nerves in the retina, resulting the passage of a neural output to the optic nerve and brain. Thus phosphenes are themselves not necessarily the goal, but are instead a marker indicating an electric field sufficient to trigger the action potential has been created at a particular location. For purposes of therapy, it is believed that the triggering of these action potentials may be useful to preserve or invigorate neural capability in the region of the maculae, reversing or arresting progress of macular degeneration, for example, or addressing various other maladies of the eye. However, it may not be necessary to actually observe the phosphenes for therapy to have an intended/desirable effect. Therefore sub-partial-field phosphene threshold therapies and/or sub-full-field phosphene threshold therapies may be desired. Devices, systems, and user interfaces geared to use in providing ocular therapy by the application of electric fields (via current or voltage controlled, or other electrical outputs) are thus desired.

This overview is intended to provide an introduction to the subject matter of the present patent application. It is not intended to provide an exclusive or exhaustive explanation, nor to describe each embodiment or every implementation of the present disclosure. The figures and the detailed description which follows more particularly exemplify these embodiments.

DESCRIPTION

Figure 1:
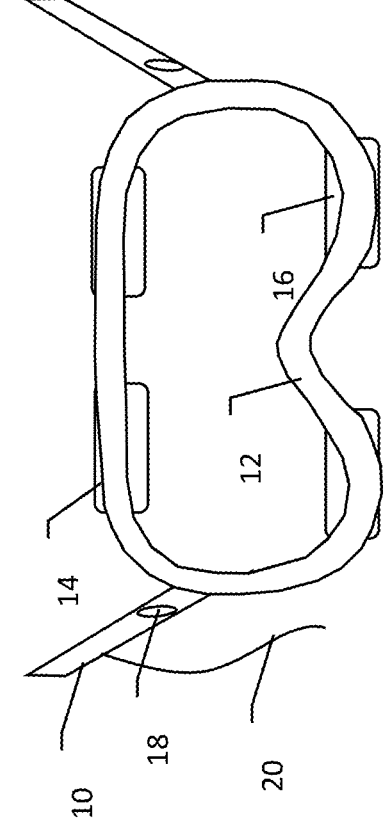
FIGS. 1-2 show an illustrative wearable therapy apparatus from the front and rear, respectively.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

Figure 2:
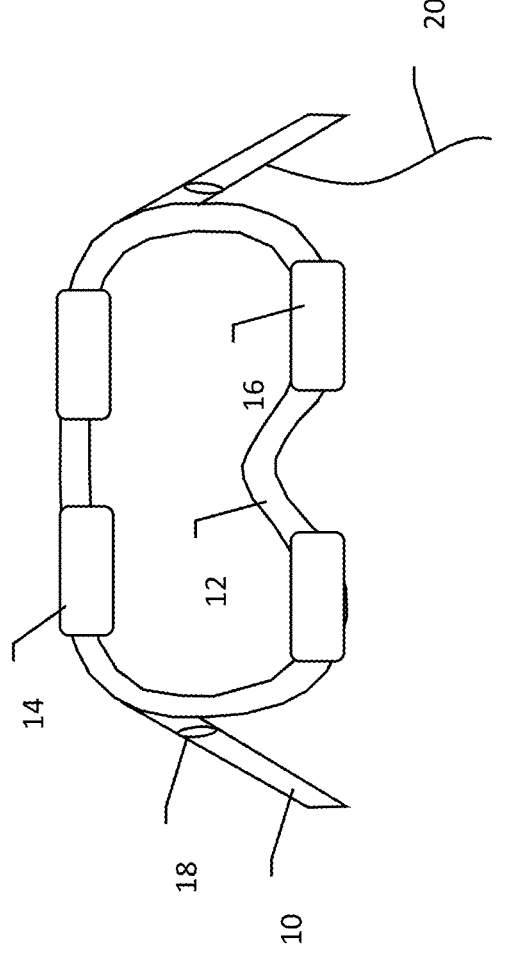

FIGS. 1-2 show a wearable therapy apparatus from a front view and a rear view, respectively. The apparatus includes arms 10 shaped and configured to rest on the ear of the patient. The arms 10 may also wrap around the ear for additional support, if desired. A front portion or eyepiece 12 carries upper pads 14 and lower pads 16, and is coupled to the arms 10 with a pivot or hinge 18. A wire connector 20 extends from the apparatus, for coupling to a pulse generator (PG), an example of which is further shown below. The PG may be carried by the patient and/or carried on a harness, neckpiece, lanyard, clothing article, or attachable to patient clothing, if desired, or carried on or by the patient in any suitable manner; a PG may be placed on a table next to the patient if desired as well.

The pads 14, 16 may be, for example and without limitation, foam pads. Some of the pads 14, 16 may also carry a conductive electrode thereon for placement against the skin of the user. The conductive electrode may include any suitable biocompatible and/or non-toxic material, such as gold, titanium, stainless steel, etc. In some examples, only the upper pads 14 are included, and each of the upper pads in such examples carry an electrode therein. In some other examples, all pads 14, 16 are included and all carry electrodes, or only the upper pads 14 carry electrodes, or only the lower pads 16 carry electrodes. Further alternatives may include only the lower pads 16, which carry electrodes in such an alternative. A nosepiece may be included if desired, in addition to or as an alternative to the lower pads 16 being present. In other examples the eyepiece 12 may rest against the nose of the user.

Optionally, the pads 14, 16 may be wettable or may carry or absorb, for example, a hydrogel, saline, or other fluid/liquid/gel for use in reducing tissue interface impedance. With a wettable pad 14, 16, the electrode therein may not need to contact the skin, for example, reducing potential skin sensations if desired. The pads 14, 16 may be reusable, removable and/or replaceable, such as by having daily, weekly, or monthly use pads that are to be replaced from time to time. The pads 14, 16 may be adjustable relative to the apparatus/eyepiece 12 to tailor fit to the user. In some examples, the eyepiece 12 may be custom fit to the user, such as by taking an image of a patient/user's face and 3D printing or otherwise custom manufacturing to the user. In some examples, the eyepiece, pads 14, 16, and/or retaining structures that hold the pads 14, 16, may be a heat-settable material that can be shaped to the face of the user and then heat-set, or UV cured to retain the shape applied thereto. In other examples, the eyepiece 12 may come in a range of sizes and/or shapes to allow a best fit to the selected.

The hinge 18 may allow the arms 10 and eyepiece 12 to be positionally adjustable to ensure fit and/or comfort to the user. Optionally, the hinge 18 may be configured to be released/loosened, adjusted, and then secured/tightened once a desirable angle is set. The hinge may be omitted in some examples.

In some examples, a pulse generator may instead be built into the eyepiece and/or into the arms or attached to the portion resting or wrapping about the ear of a patient, rather than including the wire 20. The wire 20, if used, may be on either side of the device. In some examples the wire 20 may extend out of the back end of the arms 10 so as to wrap around behind the ear of the user, conveniently keeping the wire 20 out of the way.

The eyepiece 12 may include slots, detents or the like to allow lenses to be snapped into place therein, for example, corrective lenses, polarized lenses, or lenses suited to therapy purposes such as eye exercises. In still further alternatives, the eyepiece may include built therein, or in the openings for the eyes, view screens similar to those used for virtual reality goggles to allow the user to exercise the eyes, or to experience entertainment, such as watching a movie, during therapy.

As can be observed, the upper pads 14 are positioned to rest on the forehead of the user. The position on the forehead may be located superior to the eyebrows, if desired, and inferior to the hairline. The position on the forehead may be approximately at or above the lower margin of the frontal bone. In some examples, the position may be about 0.5 to about 2.5 centimeters superior to the lower margin of the frontal bone. The upper pads 14 may be positioned to align more or less with the center of the left and right orbits, respectively, though positions more lateral or medial may be used if desired. The lower pads 16 may also be positioned to align more or less with the center of the left and right orbits, and are positioned approximately about 0.1 to about 2 centimeters inferior to the upper margin of the maxilla. In some further examples, a strap may be added to wrap around the head and elastically press the eyepiece against the face of the user, if desired.

Figure 3A:
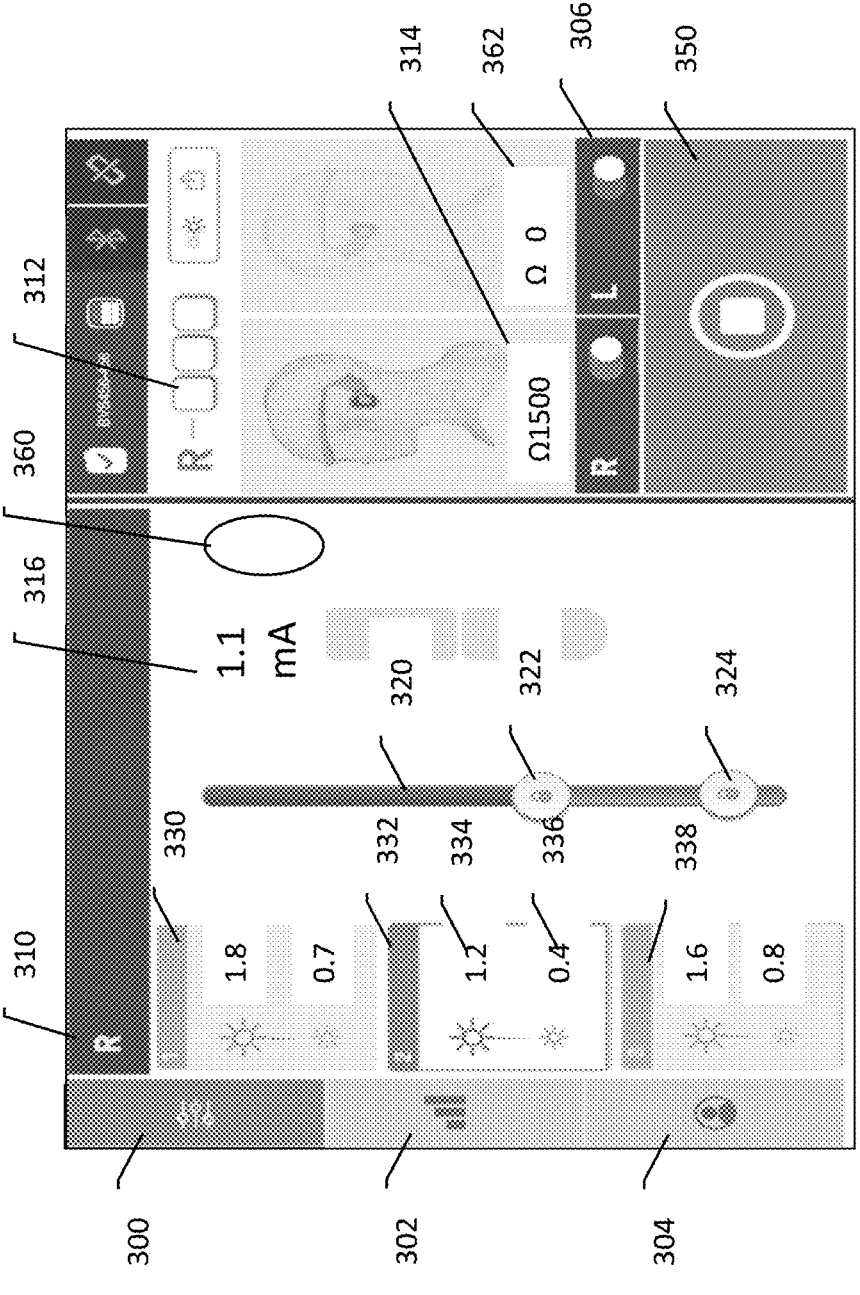
FIGS. 3A-3B show illustrative user interfaces.

FIG. 3A shows an illustrative system controller user interface. The interface may be provided on a pulse generator or on a separate physician controller. The user interface includes selectable tab on the left-hand side, with tab 300 for controlling therapy parameters, tab 302 for reviewing therapy utilization, and tab 304 for other system functions. Tab 304 can be used to select and initialize communication with the pulse generator, and may be omitted if the user interface is on the pulse generator itself. Tab 304 may instead be used to select and initialize communication with a remote server, if desired, such as by use of WiFi, Bluetooth or cellular communications (or other communications mode), allowing data, control parameters, and/or software updates to be remotely managed, retried, downloaded and/or uploaded.

In FIG. 3A, tab 300, for controlling therapy parameters, is shown. The user interface as shown at 306 includes selectors for choosing to control left or right eye parameters. In the example, the parameters for the right eye are shown, as indicated at 310. Two options are provided for entering/selecting therapy parameters in this example, with amplitude selectable on a slider 320 or using digital entry at 312. Other examples may also allow the user to select width, pulse repetition rate, polarity switching options, and/or electrode selection, though these options are not shown in this example. The interface as shown offers three different programs, as indicated at 330, 332, and 338, where the programs are pre-configured for use and each selectable by the physician. For example, the programs 330, 332, 338 may include one or more of the following, and/or variants thereof:

A 20 Hz fixed therapy: here, therapy has a single phase lasting, illustratively, for 20 minutes (longer or shorter may be used, anywhere from 1 minute to 100 minutes, or more or less as desired). The therapy output may be delivered at 20 Hz ($\frac{1}{20}$ of a second, or 50 milliseconds (ms)), by issuing a 25 ms duration pulse, followed by 25 ms of quiescent time. Every 500 ms, the output polarity switches. The amplitude of therapy can be fixed throughout the duration of the single phase, though in other examples, amplitude may vary, such as by including an initial ramp in which the amplitude starts near zero, and then raises to the selected therapy amplitude over the course of several pulses. In another example, the first pulse of each 500 ms block of pulses at a given polarity can be reduced in amplitude compared to other pulses in the block, such as by using a reduced amplitude in the range of about 10% to about 90%. The nominal amplitude for therapy pulses may be selected to be above, at, or below a phosphene threshold for the patient, for example. Use of equal ON and OFF periods (here, 25 ms ON and 25 ms OFF) is illustrative; the ON period may have a lesser or greater duration than the OFF period as long as the pair adds up to the period of the therapy in this and any other examples. Pulse width can be varied within the therapy sequence if desired.

A multi-phase stimulation pattern. Here, a series of phases of therapy are delivered. Each phase includes a series of alternating blocks of therapy output, where blocks of therapy are issued with alternating polarity from one block to the next block. Within each block a therapy pattern, with pulses having a fixed duration, followed by a quiescent period, is delivered. In an example, each phase is used for a period of time, and each phase has a different definition of one or more of the duration of blocks, or pulse durations. Amplitude may be fixed throughout the program, or amplitude may vary from one phase to another, or within a phase, or from one block to the next, or within a block from one pulse to another, as desired. In an example, the phases are as follows:

Phase 1 lasts for 1 minute, with 500 ms blocks alternating polarity, having 2 ms pulses separated by 2 ms quiescent periods.

Phase 2 lasts 2 minutes, with 500 ms blocks alternating polarity, having 20 ms pulses separated by 20 ms quiescent periods.

Phase 3 lasts 7 minutes, with 500 ms blocks alternating polarity, having 50 ms pulses separated by 50 ms quiescent periods.

Phase 4 lasts 10 minutes, with 500 ms blocks alternating polarity, having 2 seconds pulses separated by 2 second quiescent periods. Phase 4 may alternatively be described as issuing a DC output for 500 ms, in alternating polarity for 2 seconds, followed by 2 seconds quiescent period.

The programs may include variants on either of these general categories of patterns. For example, the multi-phase stimulation pattern may omit or vary one or more of the above described phases. Still other examples may reorder the above phases, or use a given phase more than once within a phase pattern. As noted, the pulse width and quiescent period durations may be equal or unequal, as desired.

It should be noted that the above examples are delivered using the signals as described, without the use of a carrier signal. One or more programs may additionally or alternatively use a carrier signal in these therapy patterns. A carrier may be used by delivering the above examples as the envelope in which a signal (square wave, sinusoid, etc.) having a frequency in the kilohertz (kHz) range (such as 0.1 to 100 kHz, or higher, if desired) is delivered. For example, a 10 kHz square wave or sinusoidal carrier signal may be used to reduce electrode-skin interface impedance.

In some examples, therapy definition and control functions of the user interface are provided only on a clinician or physician programmer, and not made available on the pulse generator user interface. In other examples, therapy definition and control functions are available in the pulse generator user interface, but password protected or otherwise made unavailable to the patient/user. The physician may enable only one program, or may enable more than one program, for use by a patient. The patient may be instructed to use programs at particular times/dates, for example. In an example, one program may be used in the morning, and another program at a different time of day. In still other examples, therapy definition and control functions are made available on the pulse generator user interface to both the physician and the patient/user.

In some examples, one program may be indicated for a particular use. For example, as further discussed below, programs may be configured to provide full-field phosphenes, partial field phosphenes, or sub-threshold stimulus in which phosphenes are not observed by the patient or are only infrequently observed by the patient. Each program may be provided with a descriptive name, if desired, where the physician and/or patient may name the programs as desired, or names may be pre-set.

Returning to FIG. 3A, each program 330, 332, 338 is illustrated with two output control values as well. For example, program 332 is shown with upper boundary 334, having a value of 1.2, and lower boundary 336, having a value of 0.4. In the example shown, these numbers represent milliamps of current; in other examples, other control parameter types (voltage or power, for example) may be used, and other ranges may also be used. For example, the range may instead be from a low bound (0%, 1% for example) to an upper bound 100% of a therapy amplitude maximum that is set by the user or physician. Such a percentage range may be linear relative to current, voltage, or power, or may have a different relationship such as a decibel, logarithmic, square/square root relationship, etc., to the underlying signal amplitude. The illustrative example is configured for issuance of current controlled therapy at amplitudes of up to 2 milliamps, with resolution of 50 microamps. Other ranges may be used, as desired, and the invention is not limited to these particular parameter types or ranges.

The upper boundary 334 and lower boundary 336 may be set by a physician or may be set automatically by a program operating on the physician controller, as desired. In an example, the upper boundary 334 is set at a full-field phosphene threshold (FPT), and the lower boundary 336 is set at a partial field phosphene threshold (PPT). These terms are further explained below. In another example, the upper and lower boundaries are set relative to the FPT or the PPT, such as being below or above the selected one of the FPT and PPT by a fixed or relative amount. For example, the upper boundary may be set at 110% of the FPT, and the lower boundary may be set at 80% of the PPT. Other variants, above and below each of the FPT and PPT may be used.

Automatic programming may be facilitated by having individual pulse generators and/or clinician programmers communicate data to a central data system where parameters for therapy which are found to work for particular patients can be mapped against factors including disease state, PPT and FPT levels, frequency, pulse width, and any other therapy or individualized (patient) factors. Optimized therapy suggestions or parameters can be created and communicated to physicians for physician use, or for automatic programming by the system.

In the example, the user interface is shown with therapy being actively delivered. The indicator at 316 shows the amplitude of therapy delivery, and the impedance that delivered therapy encounters is shown at 314. The user interface also includes a stop button or icon at 350, which is visible when therapy is being delivered to the patient. Depressing the stop icon 350 causes a communication to issue to the PG to cease therapy delivery, if the user interface is on a clinician programmer; if the user interface is on a PG, therapy ceases by action of the PG itself.

The example shown illustrates therapy on for just the right eye, as indicated at 306, where the toggle for the left eye is in the off position. Both eyes may receive therapy at the same time, if desired. If both eyes are receiving therapy, then an amplitude for the left eye would be shown at 360, and an impedance would be shown for the left eye at position 362. Two sliders 320 could also be shown. Other configurations may be used.

Figure 3B:
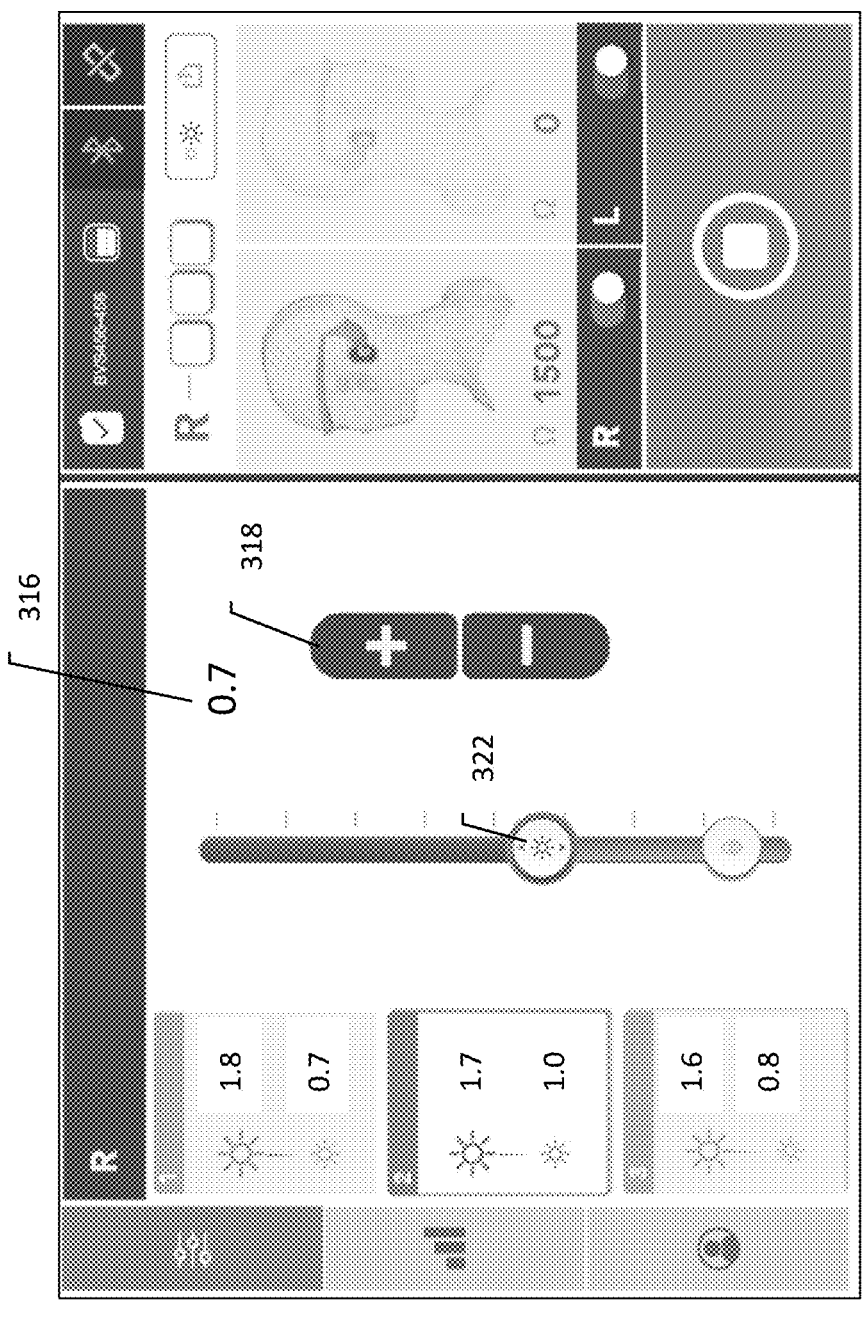

FIG. 3B shows another example. Here, the user has selected the upper icon at 322 on the slider. Doing so unlocks the icon, and an up/down control appears at 318, allowing the user to adjust the upper icon up or down, as desired.

FIGS. 4A-4I illustrate a method of phosphene testing for a patient. The user interface is different for these figures than in FIGS. 3A-3B, showing another implementation. As before, the user interface may be on a clinician programmer separate from a PG, or may be on a PG user interface. Here, a phosphene test icon is shown at 400 and can be selected for use with the left eye, as indicated at 402. A "play" button is shown greyed out at 404, and cannot be accessed until the phosphene test icon 400 is selected by the user. As can be seen, the amplitude slider bar in FIG. 4A, for the left eye, is set to a minimum amplitude and no thresholds are yet set.

Figure 4A:
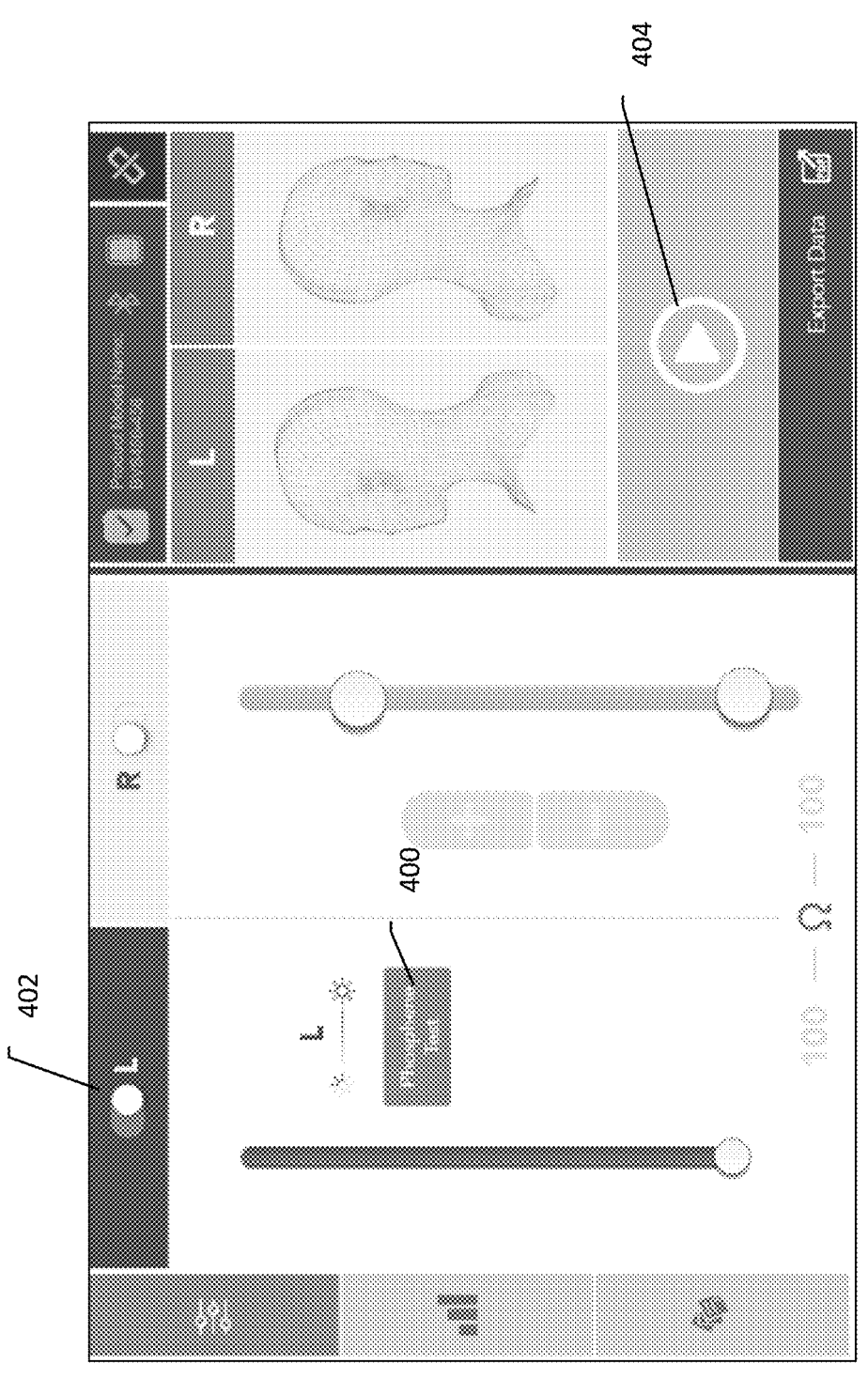
FIGS. 4A-4I show an illustrative user interface highlighting a method of phosphene threshold testing.
Figure 4B:
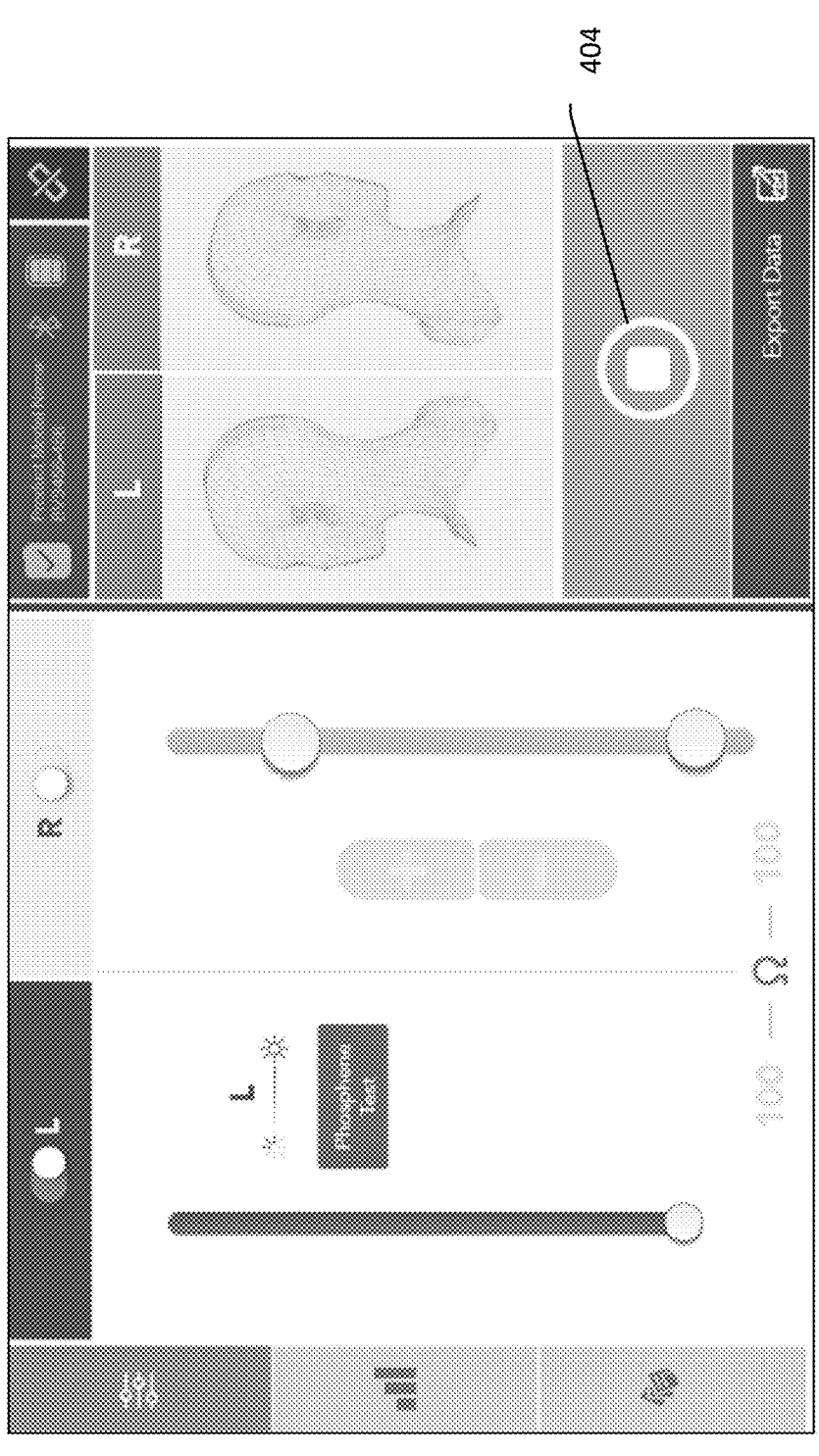

FIG. 4B shows a next step, after the icon 400 has been selected and the play icon 404 tapped. Now the icon at 404 is a pause/stop icon, and phosphene testing begins for the selected left eye. The system may begin automatically ramping amplitude up, or may ramp amplitude in response to the user tapping or holding the up/down icon 412 shown in FIG. 4C. As the amplitude increases, the slider 414 shows the changing amplitude, and a digital value is also shown as indicated at 410. The impedance that output stimuli encounters is also shown at 416. If the impedance goes above or below a preselected threshold, the system may issue an alert and/or stop the phosphene test, if desired.

Figure 4C:
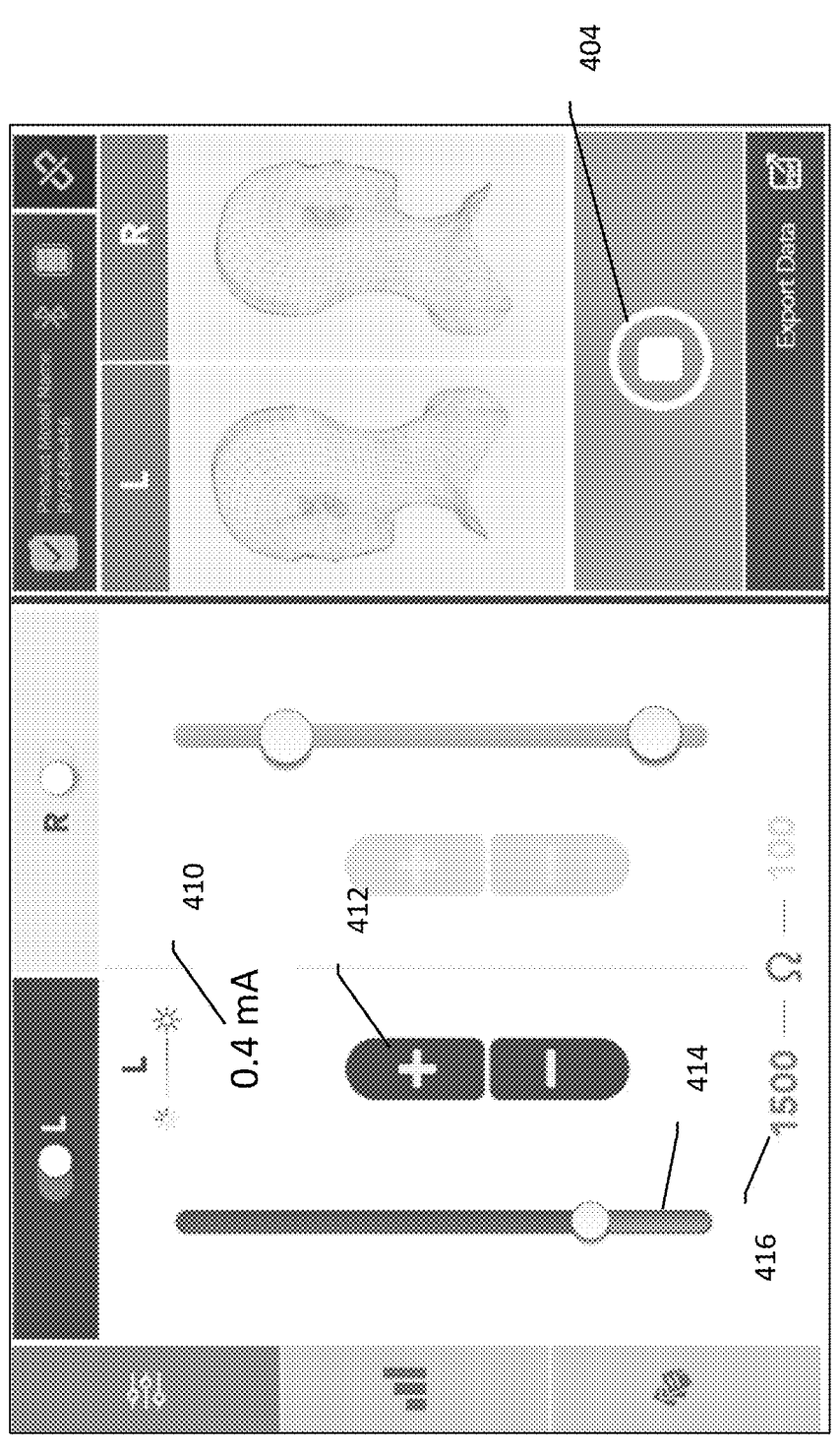

As shown in FIG. 4C, the process continues, with amplitude 410 increasing whether automatically or in response to user control 412. When the patient first observes phosphenes in the eye being tested, the user taps the slider 414 and an icon appears as shown at 420, marking the amplitude at which phosphenes are first observed. If the patient only observes phosphenes in part of the visual field, this is deemed a partial field phosphene threshold, PPT, and indicated as the PPT for the patient. The amplitude noted at 420 is then stored by the system.

Figure 4D:
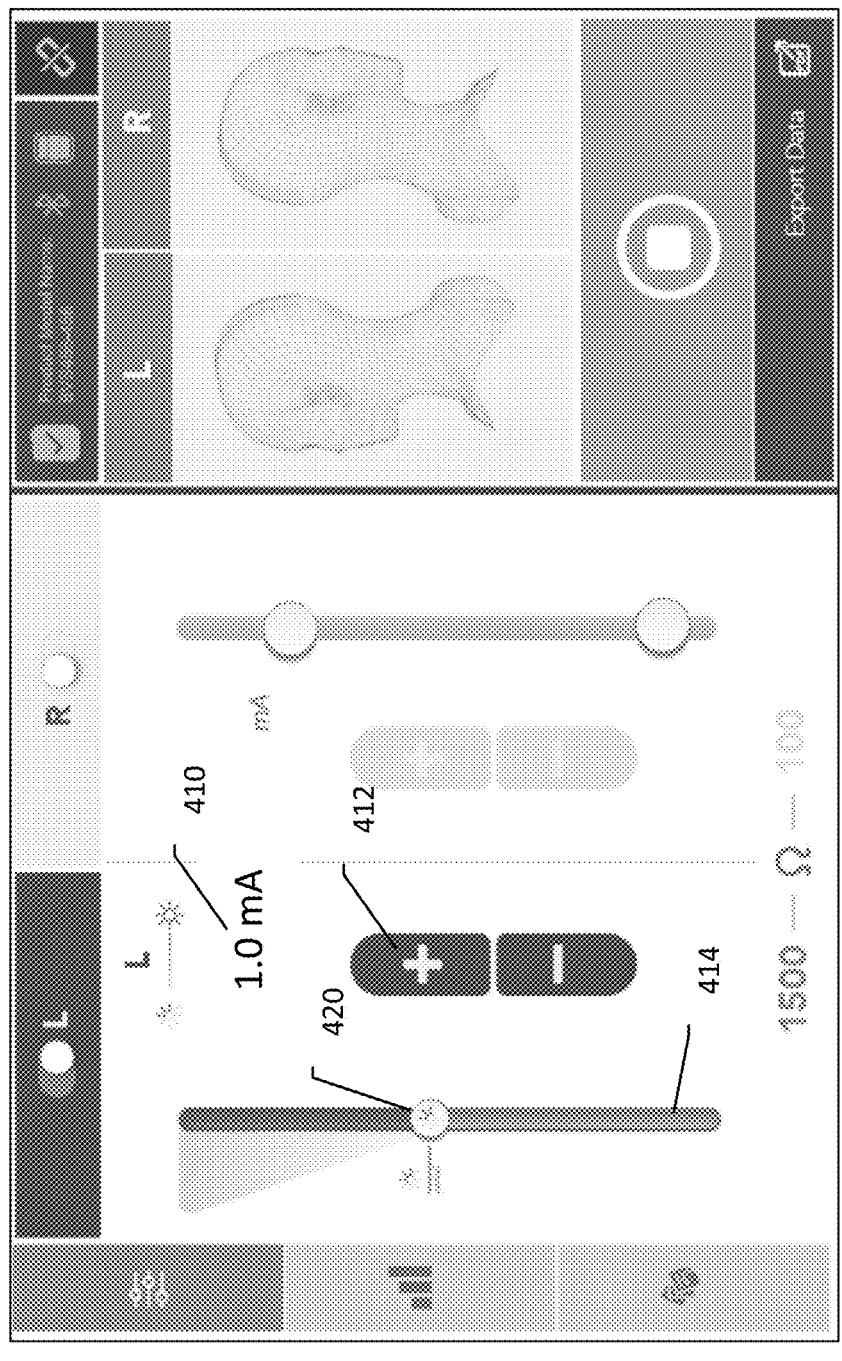
Figure 4E:
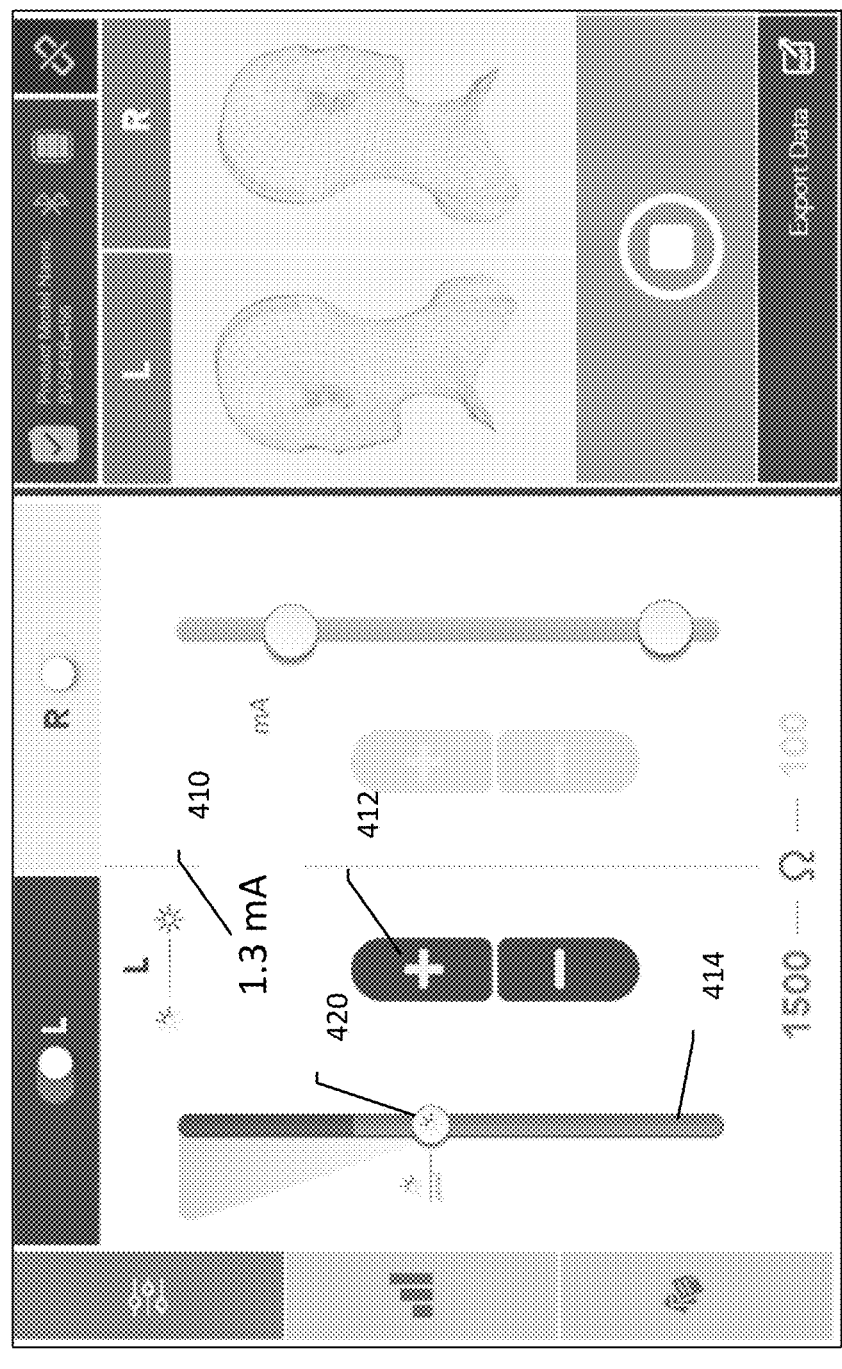
Figure 4F:
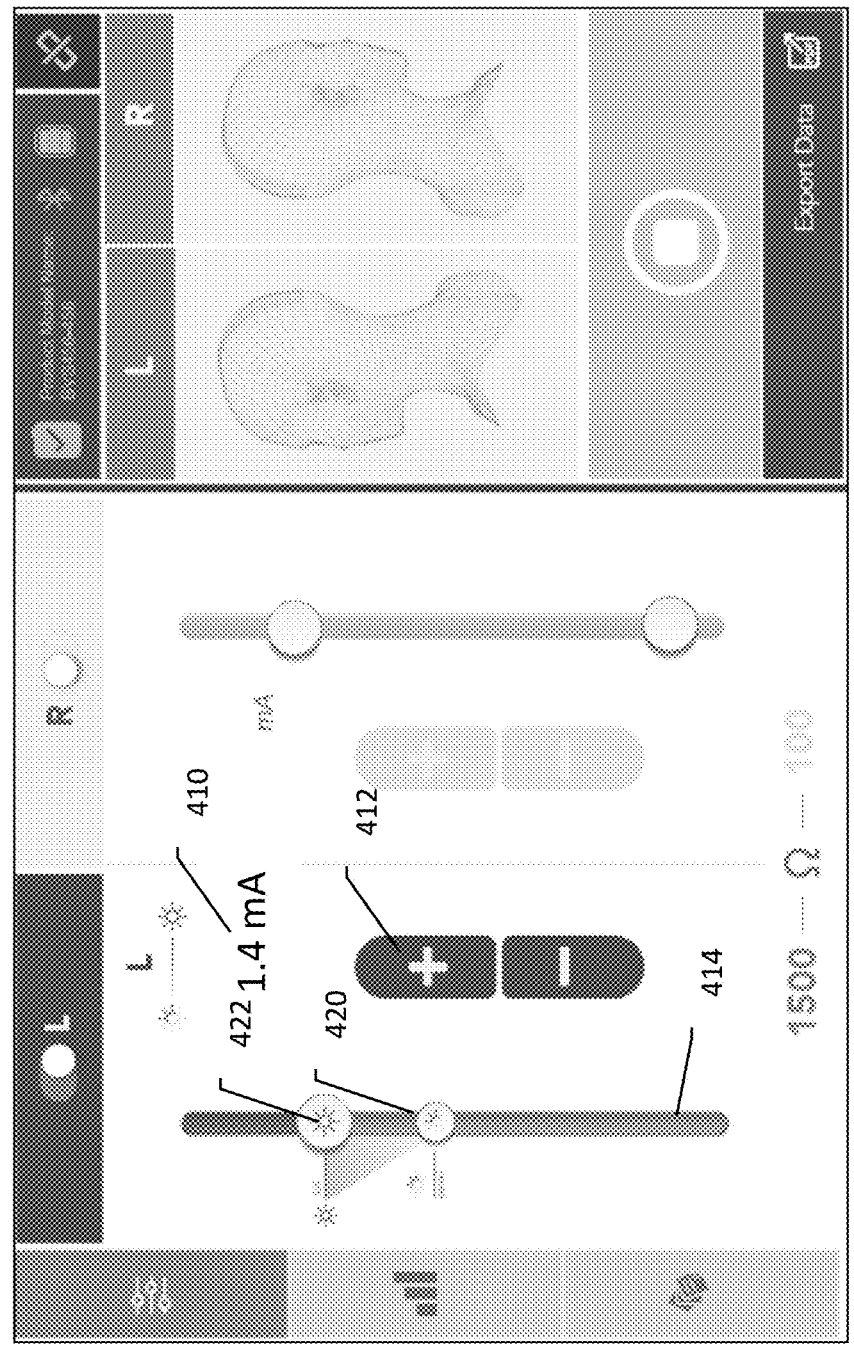

Testing may cease in some examples once the PPT is identified. In other examples, testing continues as shown in FIG. 4E, with the PPT marked as indicated at 420 and amplitude continuing to increase, either automatically or under user control 412. As shown in FIG. 4F, when the patient reports experiencing phosphenes in the full visual field, a second threshold, the full field phosphene threshold, FPT, is identified as indicated at 422. Again the value at 422 is stored as the FPT.

Testing of the eye being subjected to stimulus may stop at this point, or may further continue if desired to determine whether a still further threshold, such as a discomfort threshold, is reached, where discomfort may be defined as the experience of muscular contraction (twitching) in the region of therapy delivery, or actual reported discomfort such as heating being experienced by the patient, intense phosphenes which the patient finds uncomfortable or disorienting, or any other further effect of therapy stimuli. This further testing threshold may be omitted, as desired. The stop conditions (discomfort such as by twitching) may occur before the FPT is reached, causing the testing to cease.

Figure 4G:
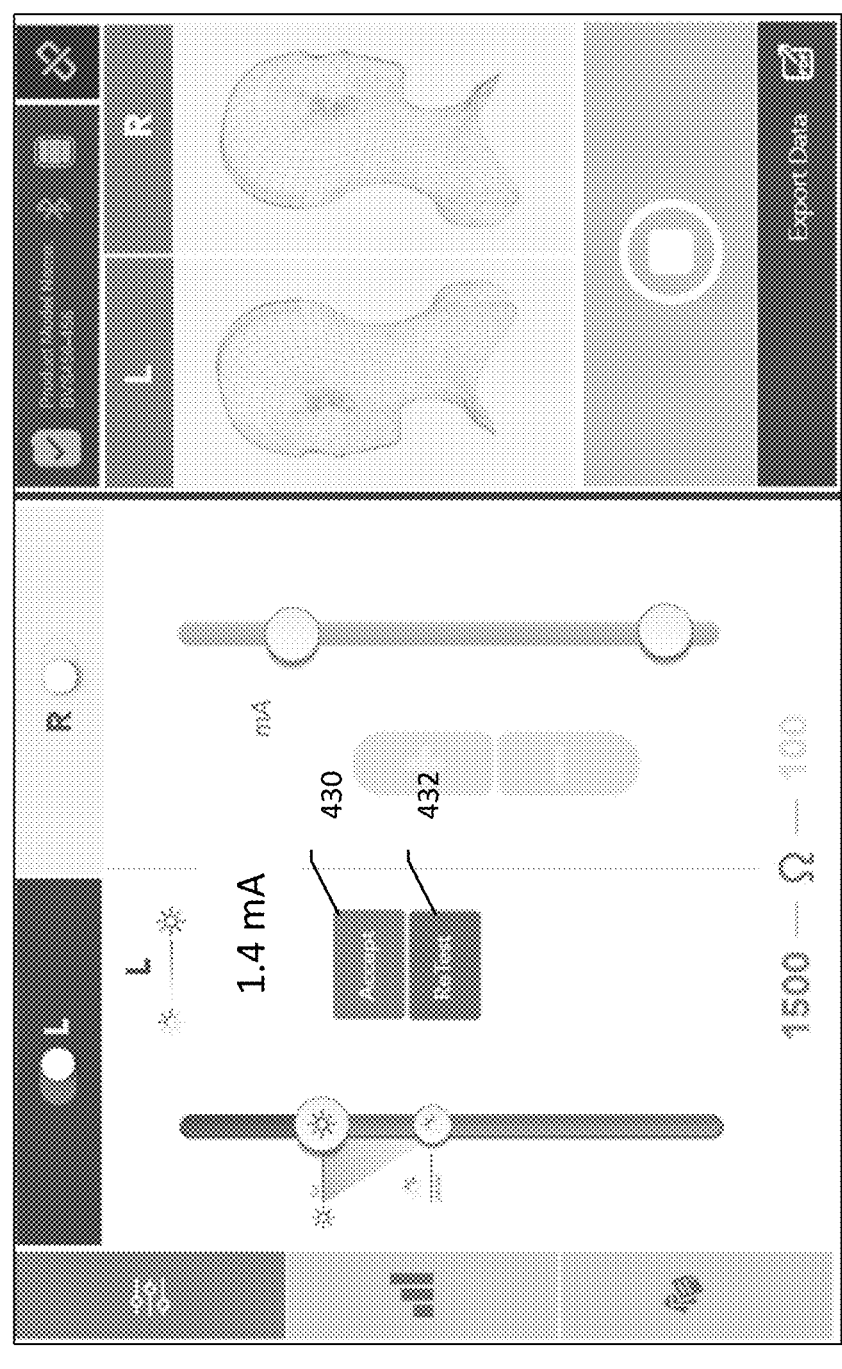
Figure 4H:
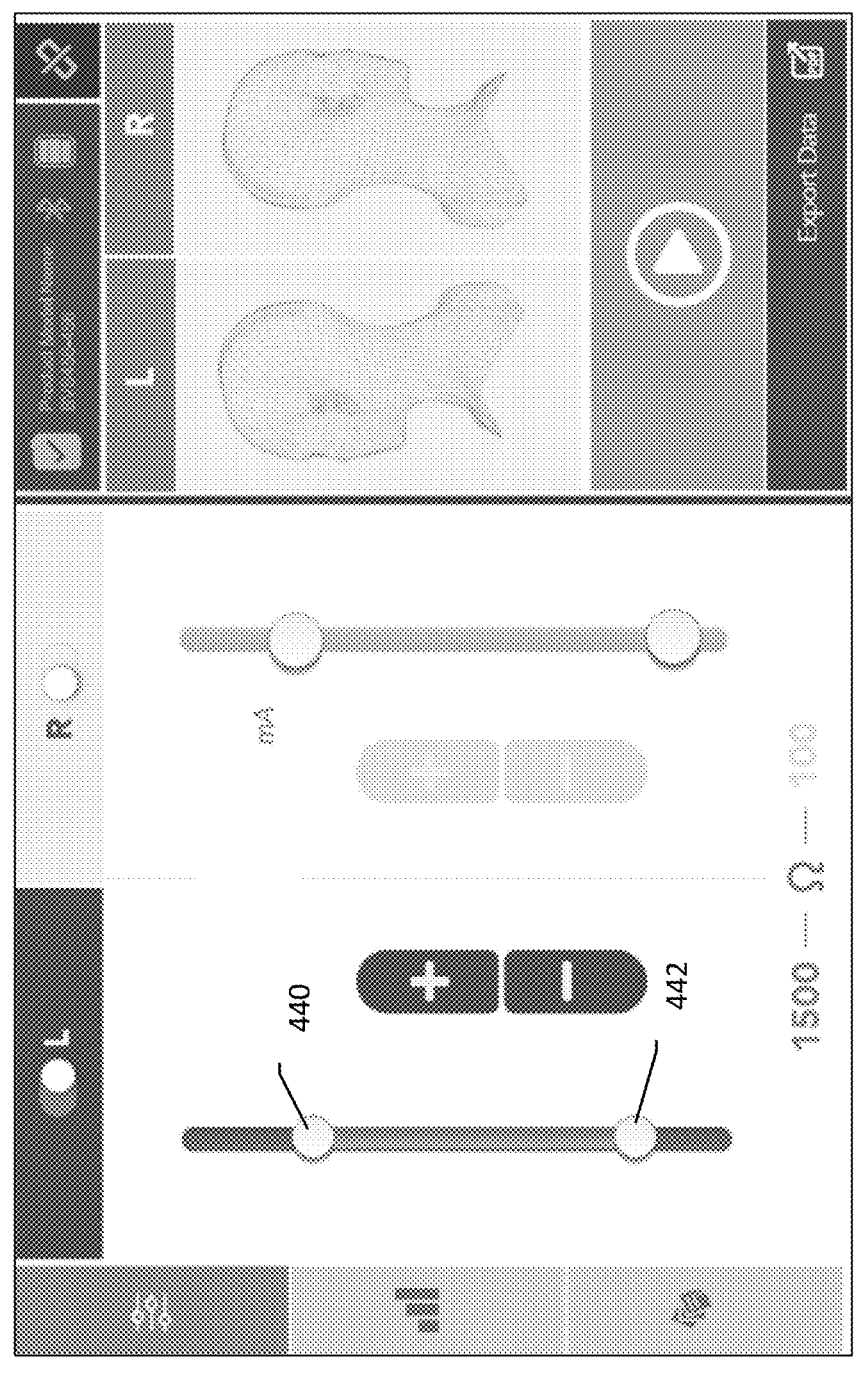

When testing of the threshold(s) is completed, the user is provided the option to accept 430 the test result, or to retest 432, as shown in FIG. 4G. In some examples, two or more tests are performed and the results averaged for each threshold, or where maximum or minimum thresholds are selected as the actual threshold for the patient. The resulting thresholds may be used to set high and low amplitude ranges, as indicated in FIG. 4H. The high boundary 440 and low boundary 442 may be, as discussed previously, set at, above, or below the PPT and/or FPT, as desired.

Figure 4I:
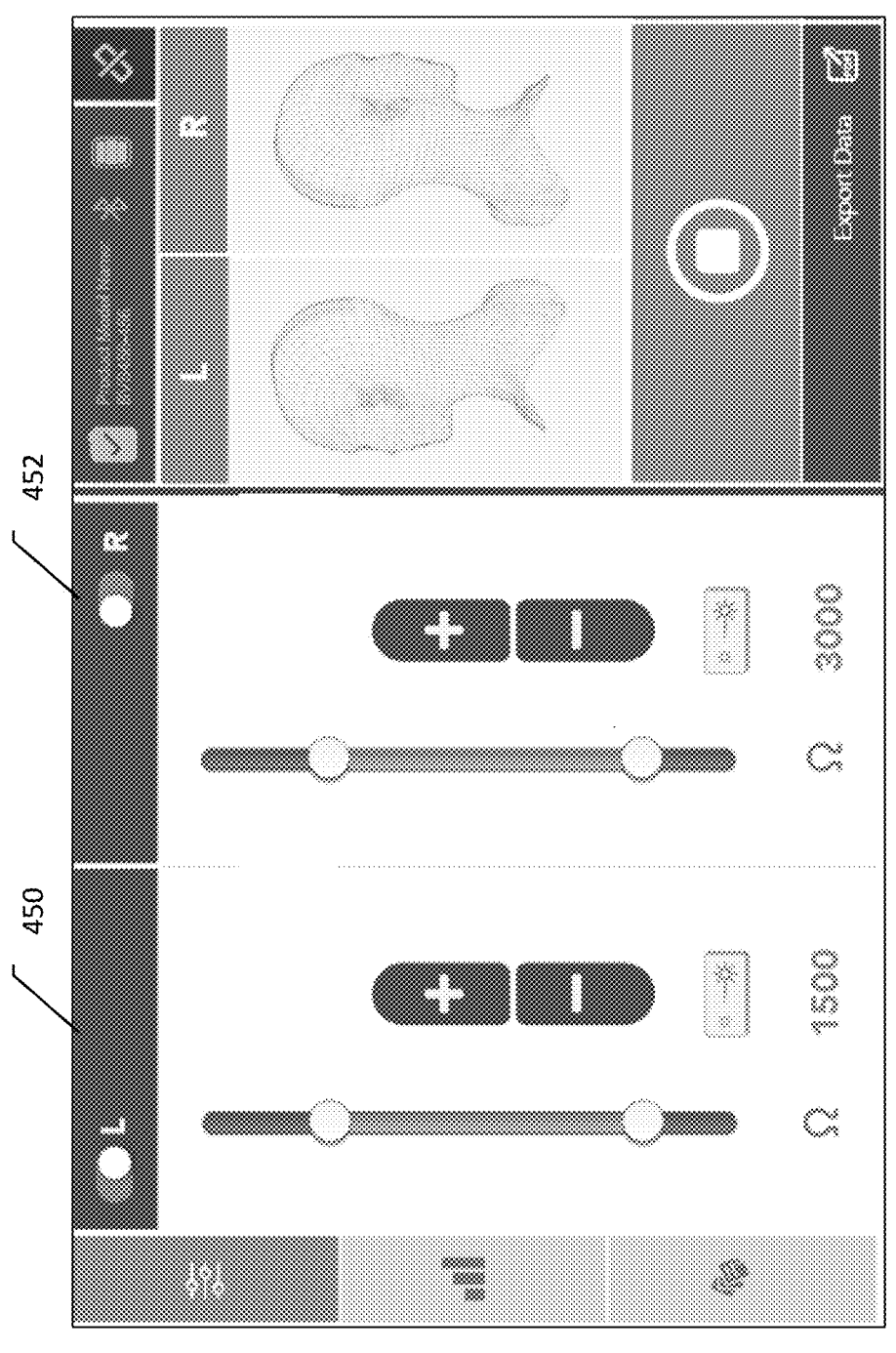

The procedure can be repeated for the other eye, as desired. The final results may be as shown in FIG. 4I. It should be noted that the scales of the amplitude sliders in FIG. 4I can be normalized/adjusted so that the available amplitude ranges are fit to the slider, if desired. Here, the final threshold settings are shown for left eye 450 and right eye 452. If performed using a clinician programmer, these results can then be programmed to the PG for use by the patient. Alternatively, if the method is performed via a PG user interface, then the results are stored to memory of the PG and, optionally, may also be communicated by the PG to another device such as a clinician device, such as a phone, tablet, computer, or printer connected by wireless (WiFi, Bluetooth, etc.) or wired connection such as a USB) connection, and/or to a remote server. In some examples the process is performed by or under physician control where the patient does not have access to the full functions of FIGS. 4A-4I, and amplitudes at which the patient is allowed to set therapy during home use can be set for each PG, specific to each eye of each patient. As will be understood, for patients needing therapy for only one eye, thresholds will be set for just the eye to be treated.

Testing can also be performed by a patient at home, if desired. As noted above and below, the patient may have full access to the user interface screens in FIGS. 3A-3B and 4A-4I in some examples. In other examples, more limited patient access is provided. In one example, the patient turns on the device, and pushes a button that increases the therapy amplitude until phosphenes are observed. Once the patient observes partial or full field phosphenes, the patient releases the button and the system automatically reduces the amplitude by a fixed amount (for example, 5-25%, or a fixed quantity). If the patient wants to check that therapy is still going, the patient may push the button again and the therapy amplitude ramps up again, but always does the automatic reduction once the button is released. That way if the patient is wondering if the system is working/on, there's an easy way to quickly check it. If the patient wants to still see the phosphenes during therapy, the patient may hold down the button until full field phosphenes are seen, or beyond, and then the reduction could still stay above the threshold. The PG would then track the amplitude at which the button is released. In an example, the patient may be prompted to perform this process both at the start of a therapy session and again at the end of a therapy session. In other examples, whether therapy should be reduced is optional to the patient after the button is released, or may be omitted entirely.

In some examples, user interfaces as shown in FIGS. 3A-3B, and the phosphene threshold testing in FIGS. 4A-4I may only be available to a physician. Such limited access may be put into effect by having these user interfaces of FIGS. 3A-3B and 4A-4I only accessible on a physician controller that is kept by the physician or clinic. Limited access may instead be provided by having, within the pulse generator, certain functions that are password protected or otherwise capable of being locked out when the physician or clinician is not present. That is, the patient-user may have a reduced set of control options in some examples compared to the physician-user. In other examples, the user interfaces of FIGS. 3A-3B and 4A-4I can be accessible in a pulse generator to all users thereof.

The user interface of FIG. 4I may also be used as a therapy delivery interface. The +/− icons shown for each of the left 450 and right 452 eyes can be used to adjust therapy between the high and low points marked on the two sliders, for example. Alternatively, therapy may be automatically set by the system (whether by the PG, a physician programmer or a patient remote control as previously discussed).

Figure 5:
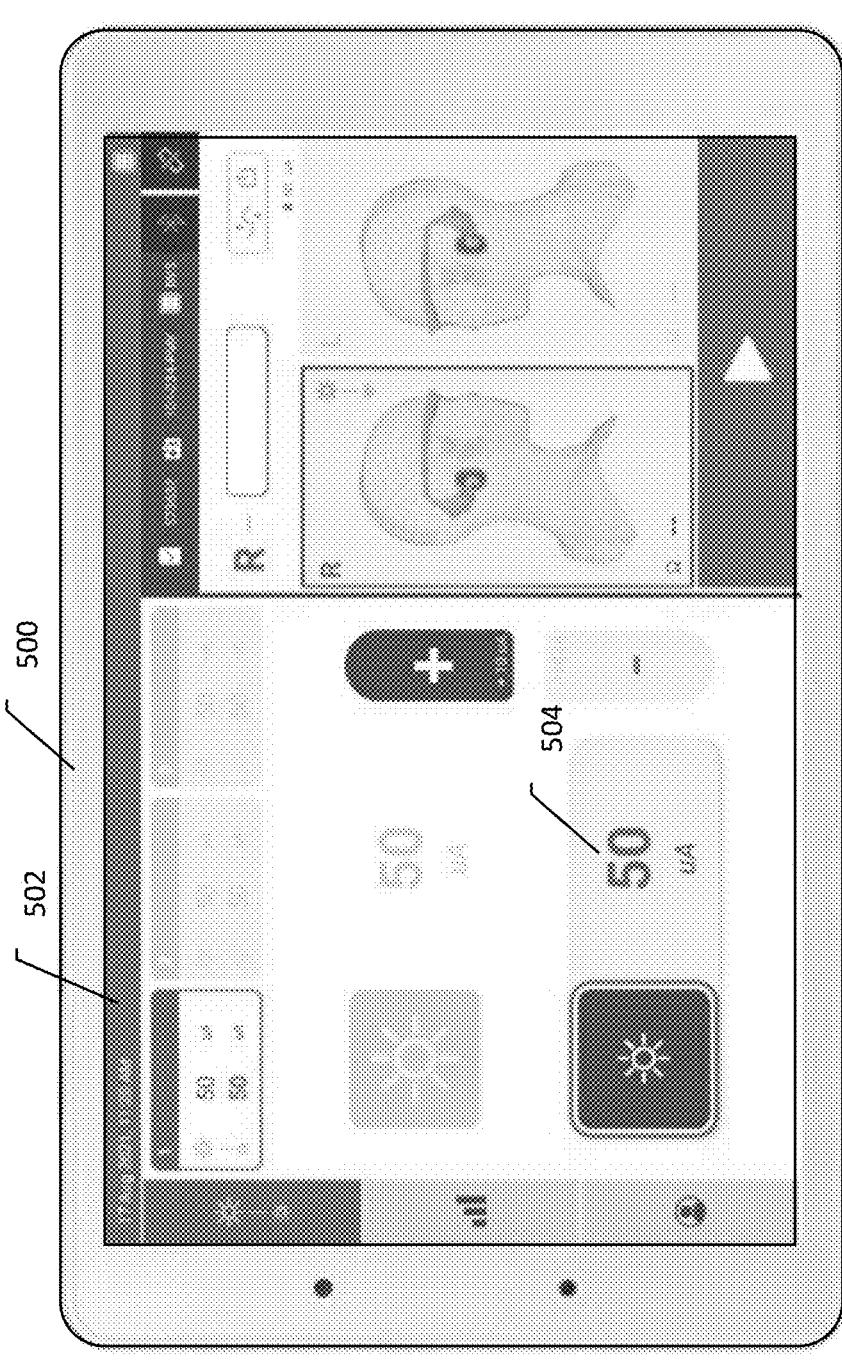
FIG. 5 shows an illustrative user interphase with therapy parameters.

FIG. 5 shows another illustrative user interface. Here, a user interface 502 is provided on the touchscreen of a mobile device, which may be a phone, smartphone, or tablet computer, for example. Outputs may be in the range of microamps, as indicated at 504. The several variants noted above may apply as well to FIG. 5. In some examples, the pulse generator user interface maybe provided by a mobile device operating in communication (Bluetooth, Wifi, Infrared, or other wired or wireless communication) with a pulse generator module; such a mobile device may be a "remote control" for the user to use, for example, and may implement the user interfaces shown in FIGS. 3A-3B and 4A-4I on a full or limited-access basis (where the patient has less access than the physician), if desired. That is, the system may have a pulse generator and a "remote control" running an application or "app" that provides controls to the user. In some examples, a patient app and a physician app may be provided, each having different levels of access to therapy controls and/or phosphene testing steps. In other examples, a single app may have different levels of access available using password or other controls.

Figure 6:
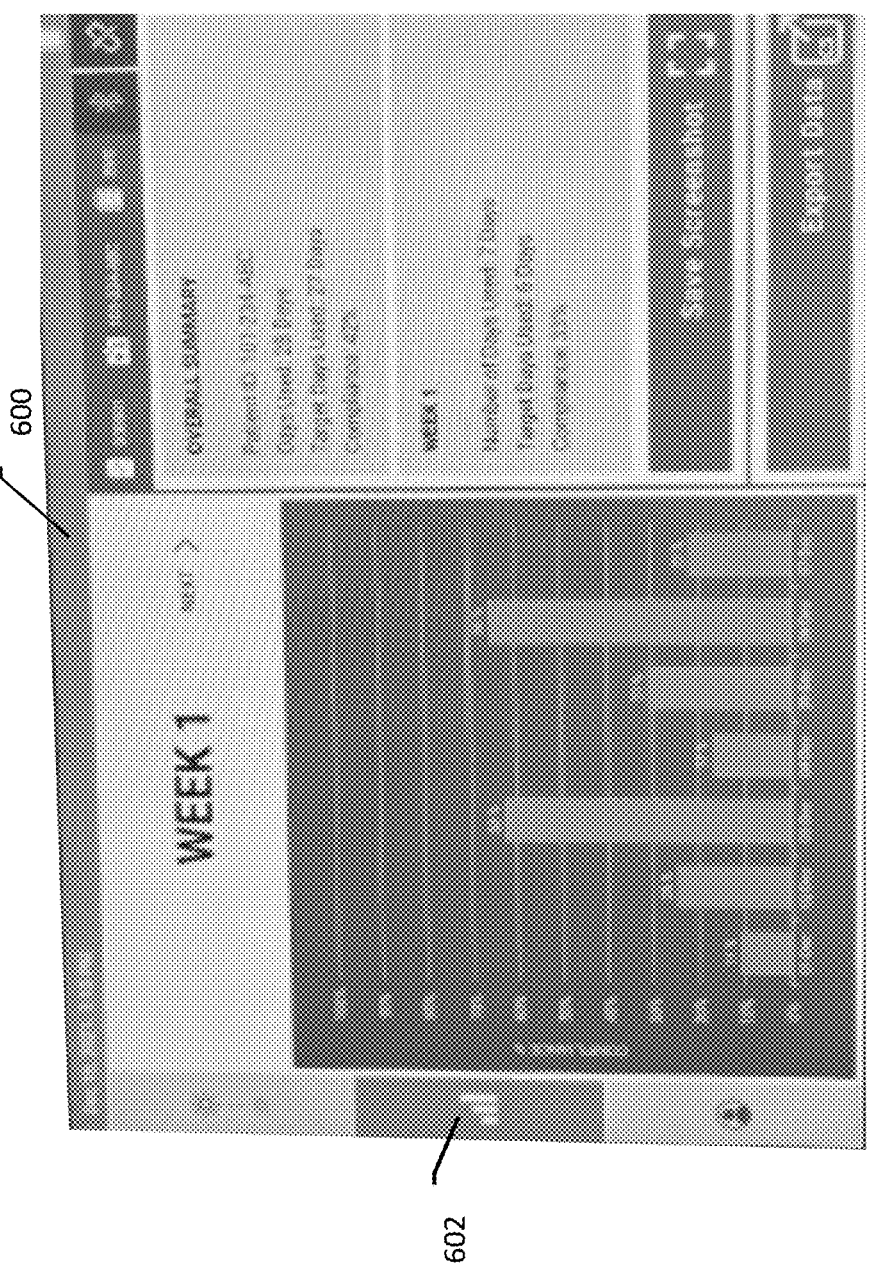
FIG. 6 shows an illustrative user interface with therapy utilization.

FIG. 6 shows another example user interface screen at 600. Here, the therapy utilization tab 602 has been selected. The patient's daily use may be illustrated, for example, across a week of therapy. In the example shown, daily use, such as in terms of delivered therapy duration, or energy, or other metric, is illustrated. The PG may store, and the user interface (PG, physician controller, remote control, etc. as discussed above) may display, for example, any of the following:

Overall Compliance %, which may be calculated as the number of scheduled therapy sessions completed, or the amount of time scheduled for therapy which is actually performed, or other metric.

Total Minutes of Therapy Completed

Total Minutes of Therapy Assigned (through current day)

Days Completed

Days Assigned (e.g.: 90)

High Impedance Errors

Programmed Current (mA) for each eye

Total charge (C), power (W) or energy (J) delivered for each eye

Other suitable metrics may be displayed, as desired. Some illustrative metrics include impedance measurements, patient self-administered phosphene threshold results, if allowed, and/or actual therapy settings selected by patients.

Figure 7A:
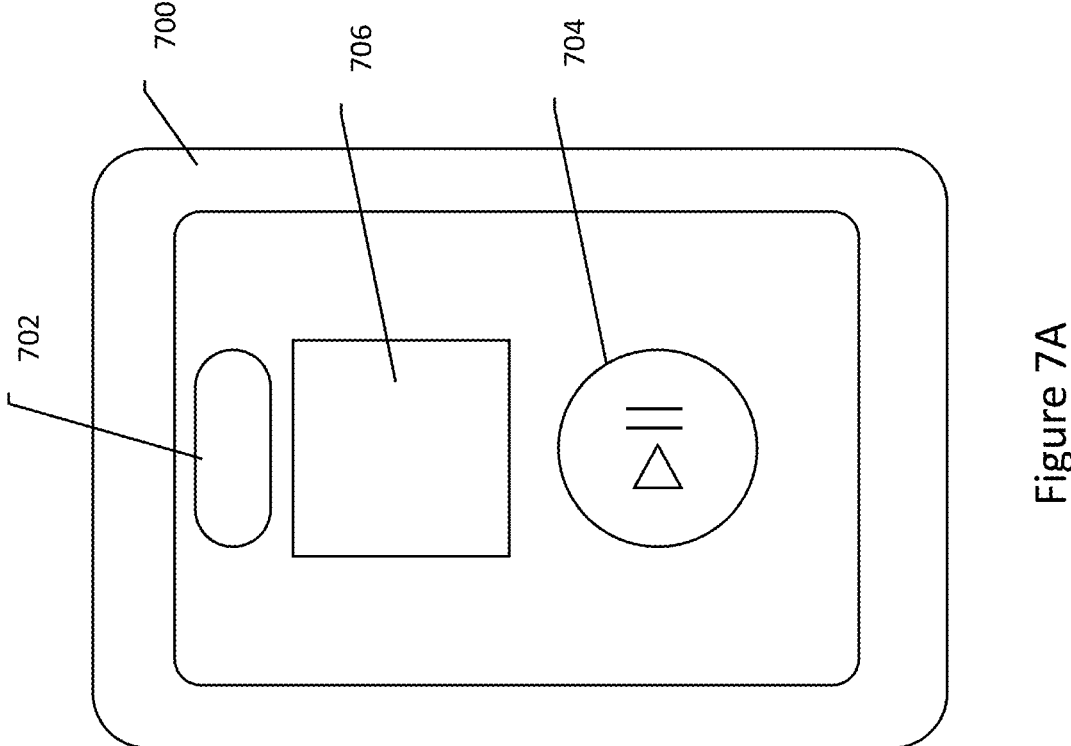
FIGS. 7A-7B show an illustrative pulse generator for a therapy system.

FIG. 7A shows an illustrative pulse generator (PG). The device is provided in a housing 700, having a power on button 702, a user interface 706 having a display screen, and a therapy on/pause/stop button 704. Additional controls, such as for selecting which eye to provide therapy to, amplitude up/down controls may also be provided, as desired. The PG may include braille or other tactile markings thereon to enable visually impaired patients to recognize each control. To the extent that a wireless pairing mode is desired (such as for Bluetooth), the PG may include an additional button on the exterior thereof, or an icon on a screen 706 to allow such pairing. Additional buttons or other controls may be provided, and the screen may be a touchscreen if desired. The user interface 706 may include a touchscreen, with or without the other controls provided as separate buttons; that is, the up/down amplitude buttons may instead be icons on a touchscreen.

Figure 7B:
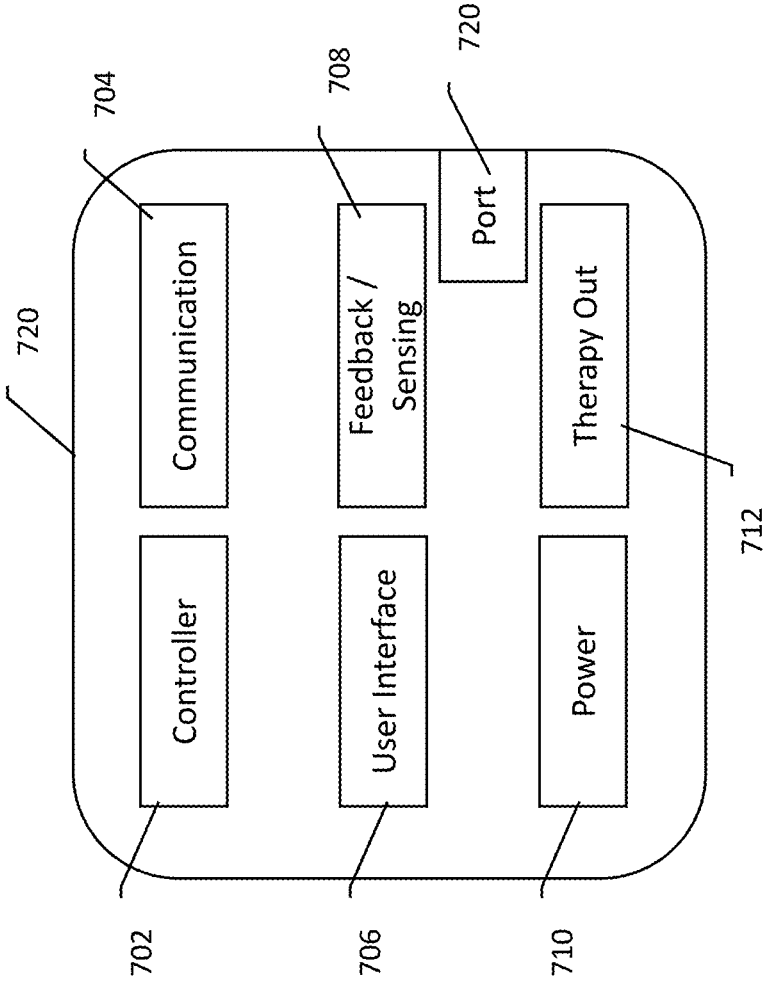

FIG. 7B is a block diagram for the circuitry within the PG. In this example, a control circuitry 702, such as a microcontroller, microprocessor, or state machine, for example and without limitation, is provided. The device may also include communication circuitry 704 (such as RF, Bluetooth™, infrared, WiFi, cellular, or other communication). A user interface 706, such as buttons, a microphone and/or speaker, screen, touchscreen, keyboard, or other user interface, is also provided. Therapy output 712 and feedback modules 708 are illustratively shown; such modules may be in the form of dedicated circuitry or may be integrated into the controller 702. Power 710 may be provided by, for example, replaceable or rechargeable batteries and/or plug-in-type power. At least the therapy output 712 and feedback sensing module 708 are configured to be coupled to a port 720 that is adapted for receiving a plug, wire or other connector from a therapy delivery apparatus, such as that shown above. Sampling circuitry, as well as filtering and/or amplification circuitry may be part of the feedback/sensing module 708, including for example, analog to digital conversion circuits. Current or voltage generating, buffering and amplifying circuits, as well as voltage step-up circuitry, may be included in the therapy output circuitry 712, to allow electrical energy taken from the power circuit 712 to be delivered in suitable therapy format. The pulse generator may include circuits, power sources, and other features as disclosed in any of U.S. Pat. No. 7,251,528, titled TREATMENT OF VISION DISORDERS USING ELECTRICAL, LIGHT, AND/OR SOUND ENERGY, US PG Pat. Pub. No. 2020-0324114, titled SYSTEMS AND INTERFACES FOR OCULAR THERAPY, US PG Pat. Pub. No. 2020-0101290 titled SYSTEMS AND METHODS FOR CONTROLLING ELECTRICAL MODULATION FOR VISION THERAPY, US PG Pat. Pub. No. 2020-0171307, titled HEAD WORN APPARATUSES FOR VISION THERAPY, U.S. patent application Ser. No. 16/900,115, filed Jun. 12, 2020, titled WEARABLE MEDICAL DEVICE, PCT Pat. App. No. PCT/US2020/039776, filed Jun. 26, 2020, titled SYSTEMS AND INTERFACES FOR OCULAR THERAPY, and/or PCT Pat. App. No. PCT/US2020/041166, filed Jul. 8, 2020, titled OCULAR THERAPY MODES AND SYSTEMS, the disclosures of which are incorporated herein by reference.

Figure 8:
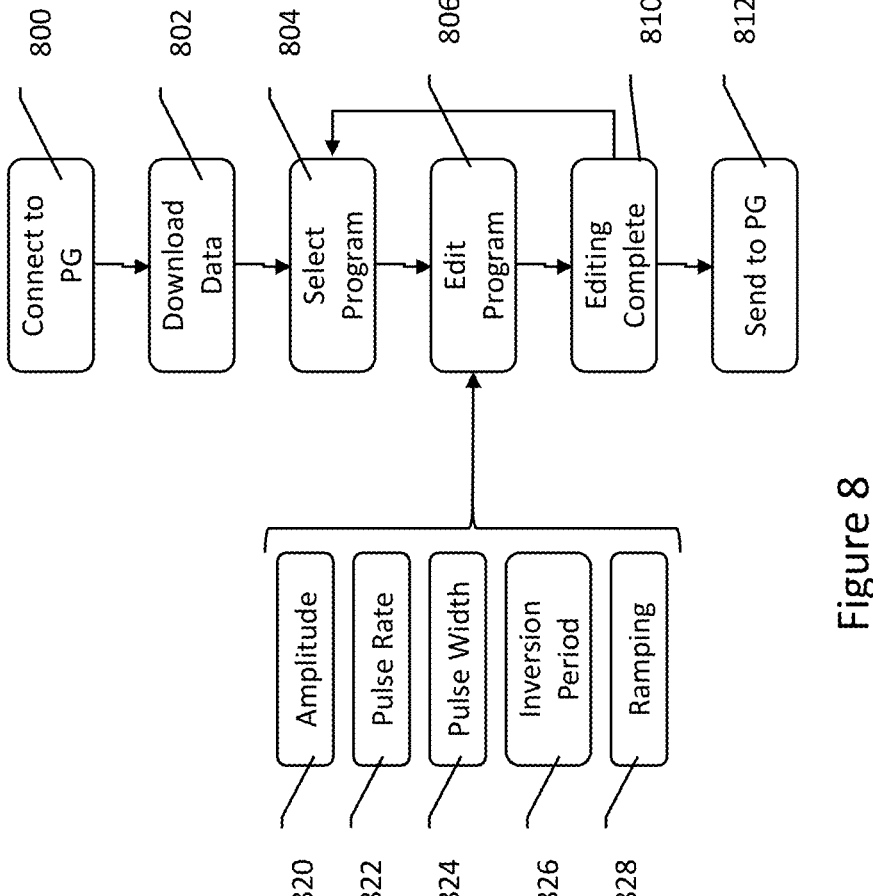
FIGS. 8-10 show process flows in block form.
Figure 9:
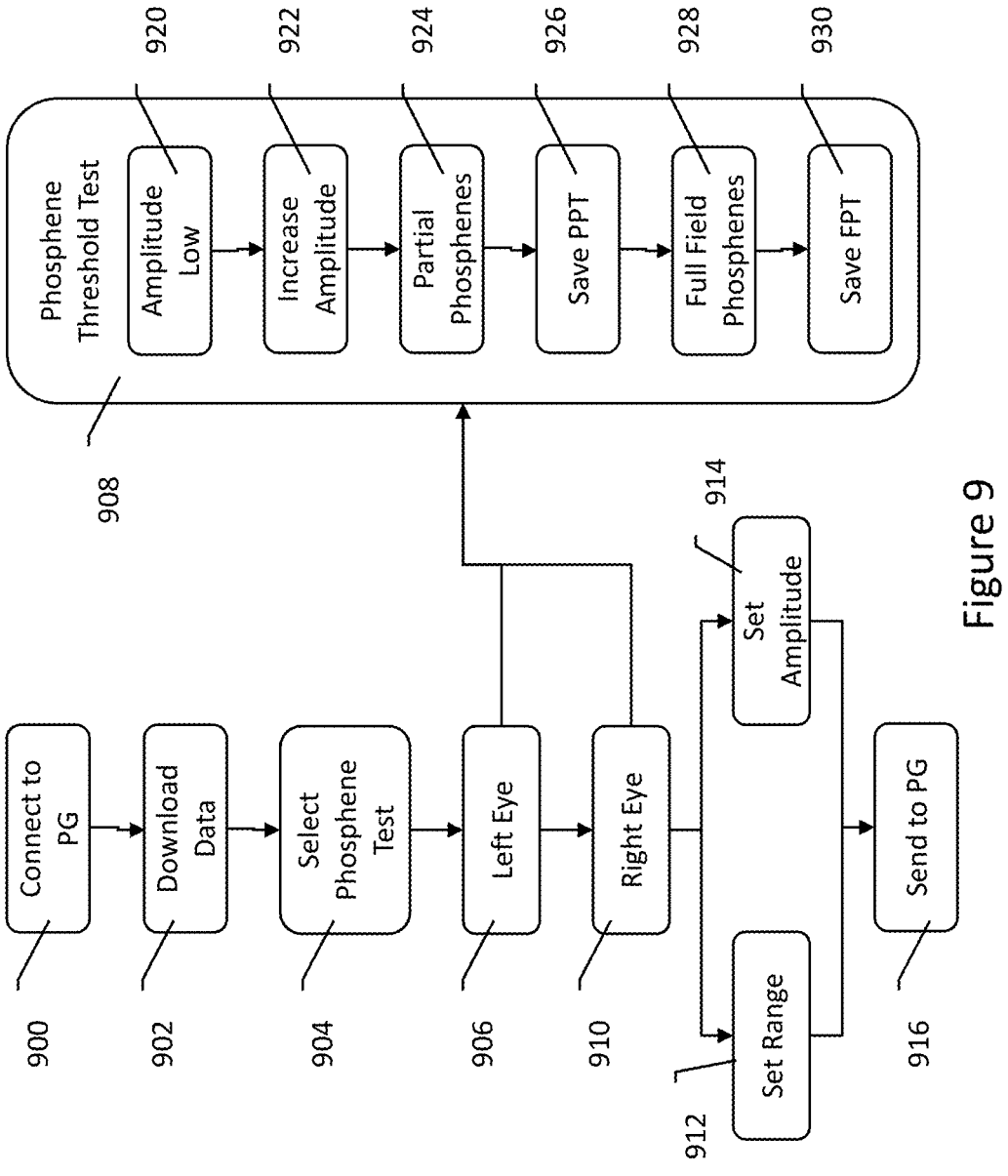
Figure 10:
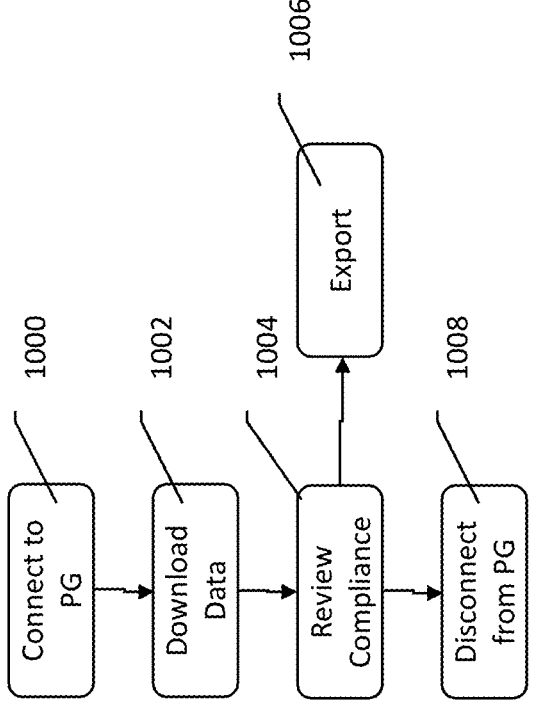

FIGS. 8-10 show process flows in block form. Starting in FIG. 8, therapy program editing is shown. A physician uses the physician controller to connect to a pulse generator (PG) at 800. This may include the use of a wireless communication method (such as Bluetooth), and selecting the PG and/or performing a pairing process. Next, data from the PG is downloaded, including for example any therapy history, patient information, and device status, as shown at 802. Blocks 800 and 802 may instead comprise a patient control device, such as a patient tablet or phone operating an app, linking to a PG and downloading data. If the user interface for program editing is provided on the PG, then blocks 800 and 802 may be omitted, if desired. The editing described can be performed a user, who may be a physician-user, or a patient-user.

A program is then selected at 804 by the user, and edited, as indicated at 806. The editing step 806 may include one or more of the various function shown to the left, including modifying amplitude 820, pulse repetition rate 822, pulse width 824, a polarity inversion period 826 (where the inversion period may mean that monopolar outputs are issued for a period of time at a first polarity, and then at the opposite polarity after expiration of the inversion period 826), and/or ramping 828 (where ramping indicates initiating therapy at a relatively low amplitude and increasing to the set amplitude 820). The user then indicates that editing is complete at 810. If more programs are to be edited, the method returns to 804. If all programs that need editing have been edited, the method concludes with the updated programming being sent to the PG, as indicated at 812. Block 812 may be omitted if the user interface is that of the PG, and instead replaced with the PG simply storing the updating program settings to memory.

FIG. 9 shows a process for phosphene threshold testing. A physician uses the physician controller to connect to a pulse generator at 900. This may include the use of a wireless communication method (such as Bluetooth), and selecting the PG and/or performing a pairing process. Next, data from the PG is downloaded, including for example any therapy history, patient information, and device status, as shown at 902. If the user interface for phosphene threshold testing is provided on the PG, then blocks 900 and 902 may be omitted, if desired. The phosphene threshold testing described can be performed a user, who may be a physician-user, or a patient-user.

A phosphene threshold test is selected as indicated at 904 among the functions available to the user. Phosphene threshold testing is performed for the left and/or right eye, as desired by the user, as indicated at 906, 910, using the steps shown to the right at 908.

The phosphene threshold test 908 is shown as starting at 920 with amplitude low. The amplitude may be in terms of any of energy, current, power, or voltage control. The amplitude is increased 922, either automatically or under direct control of the user. When the patient observes phosphenes initially, this can be termed a partial field phosphene event, as indicated at 924. The PPT is saved, as indicated at 926, and the amplitude is again increased automatically or under user control, until the patient observed full field phosphenes, as indicated at 928. The FPT is then saved, as indicated at 930. It may be possible that no PPT is observed and the patient only observes the FPT, in which case blocks 928 and 930 may not occur as the method can terminate with the patient either reaching a maximum amplitude, a timeout, or indicating discomfort with increasing amplitudes.

The user can then configure PG output parameters. In some examples, the patient may be allowed to exert a degree of control, for example, by having the physician set a therapy output range, as indicated at 912, between high and low boundaries for example. The patient can then be free to increase or decrease therapy amplitude between such boundaries. In other examples the patient may be allowed to change other parameters, such as pulse width, duty cycle, frequency/pulse repetition rate, therapy duration, etc. by having full access to therapy controls. Alternatively, the physician may set a amplitude 914 for use in therapy, where the amplitude set 914 may be specific to each of several programs, or may be used across all programs, as desired. The parameters, once set, are sent to the PG, as indicated at 916 or, if the PG provides the user interface for phosphene threshold testing, the parameters are then stored by the PG itself. In other examples the range setting or amplitude setting steps 912, 914 may be performed automatically, if desired, using an underlying program/algorithm for settings thresholds. The steps at 912, 914 may be informed or controlled by the PPT and/or FPT as determined in the test 908.

FIG. 10 shows an example of patient metric management. Here, the physician controller again connects to a PG at block 1000, as before. Data from the PG is downloaded at block 1002, as before. If the user interface for compliance monitoring is provided on the PG, then blocks 1000 and 1002 may be omitted, if desired. The compliance monitoring described can be performed a user, who may be a physician-user, or a patient-user, though it is more likely that a physician would perform such monitoring, the patient may also find it useful to review his or her own compliance.

A set of patient compliance data, such as shown above in FIG. 6, is displayed to the physician at block 1004, who reviews it. This data may be exported at 1006 to other devices/systems, such as for use in research and development of the system. The communication session is then disconnected, as indicated at 1008. The PG may update its own memory to indicate or clear those data records that have been downloaded to the physician controller.

In the preceding, a clinician or physician may include any person who is engaged in eyecare as one who diagnoses or treats conditions of the eye; steps may also be taken by a nurse or nurse practitioner who may be, for such steps, considered a physician or clinician. Ophthalmologists and/or optometrists may fulfil the role of clinician or physician, as well as physician assistants. These terms are not intended to be, nor should be treated as, limiting in the context of the invention.

An illustrative and non-limiting example takes the form of a method of vision therapy comprising presenting, on a user interface, an option to select a phosphene test to perform. Such a step is illustrated by block 400 in FIG. 4A. The method also includes receiving a selection of the phosphene test, again as illustrated at 400 in FIG. 4A. The method includes presenting, on a user interface, an option to select the right eye or the left eye as a first eye for testing. The toggle or selector switches at 402 in FIG. 4A allow selection. The method includes executing the phosphene test on the first eye by delivering an output stimulus to the region of the first eye starting at a first amplitude, and increasing the amplitude of the output stimulus, and receiving a first indication of partial field phosphenes being observed by the patient. FIGS. 4C and 4D illustrate the increasing amplitude, which can be automatic or manually increased, and marking of an amplitude at 420 for partial field phosphenes threshold. The method includes storing a second amplitude upon receipt of the first indication as a partial phosphene threshold, as noted relative to 420. The test may proceed by continuing to increase the amplitude of the output stimulus until at least one of: identifying a stop condition; or receiving a second indication of full field phosphenes being observed by the patient. A stop condition may include reaching a maximum amplitude or the patient indicating some other reason to stop, such as the stimulation becoming uncomfortable. The second indication is illustrated in FIG. 4E at 422.

Additionally or alternatively, the continuing to increase step can be performed until receiving the second indication, and the method further comprises storing a third amplitude upon receipt of the second indication, as is noted in relation to 422 in FIG. 4E.

Additionally or alternatively, therapy can be delivered using one or more of the phosphene thresholds, such as by placing the amplitude of therapy between the partial field and full field phosphene thresholds. For example, amplitude ranges can be set and stored or communicated as indicated in FIG. 9 at 912/916.

The method can also include delivering a therapeutic output stimulus to the first eye having an amplitude below the second amplitude; receiving an input from the patient requesting to confirm therapy; increasing the amplitude of the therapeutic stimulus above the second amplitude; receiving an input from the patient confirming occurrence of phosphenes while the amplitude is increased above the second amplitude; and returning to delivering the therapeutic output stimulus having an amplitude below the second amplitude. In one example described above, the patient simply pushes an amplitude increase button or icon, the system responds by increasing amplitude, and when phosphenes are observed, the patient releases the button or icon. Alternatively, the patient can push and release an icon or button, and then later push the same or a different icon; it may be easier with low-vision patients to simply push and hold until the phosphenes are observed.

Additionally or alternatively, the method may be repeated for the other eye after a first eye undergoes phosphene testing and threshold storing. For example, the method may include, after executing the phosphene test on the first eye, executing the phosphene test on a second eye of the patient by: delivering an output stimulus to the region of the second eye of the patient starting at the first amplitude, and increasing the amplitude of the output stimulus; receiving a third indication of partial field phosphenes being observed by the patient; storing a fourth amplitude upon receipt of the third indication as a partial phosphene threshold; and again continuing to increase the amplitude of the output stimulus until at least one of: identifying a stop condition; or receiving a fourth indication of full field phosphenes being observed by the patient. Further in this alternative/addition, the again continuing to increase step is performed until receiving the fourth indication, and the method further comprises storing a fifth amplitude upon receipt of the second indication.

Therapy can be delivered after the phosphene test(s) are complete using an apparatus as in FIGS. 1-2. That is, the method may include delivering a therapeutic output stimulus using a therapy delivery apparatus having an upper right electrode, a lower right electrode, an upper left electrode, and a lower left electrode, the therapy delivery apparatus being wearable on the face of the patient such that the upper right electrode is located above the right eye, the lower right electrode is located below the right eye, the upper left electrode is located above the left eye, and the lower left electrode is located below the left eye, by issuing a first therapeutic output stimulus having an amplitude between the second amplitude and the third amplitude and issuing a second therapeutic stimulus having an amplitude between the fourth amplitude and the fifth amplitude as follows: if the first eye is the patient's right eye, issuing the first therapeutic stimulus using the upper right electrode and lower right electrode and issuing the second therapeutic stimulus using the upper left electrode and the lower left electrode; and if the first eye is the patient's left eye, issuing the first therapeutic stimulus using the upper left electrode and lower left electrode and issuing the second therapeutic stimulus using the upper right electrode and the lower right electrode.

Additionally or alternatively, the output stimulus is generated by a pulse generator, and the user interface is part of the pulse generator. Additionally or alternatively, the output stimulus is generated by a pulse generator, and the user interface is part of a programmer, the programmer being in communication with the pulse generator.

Another illustrative and non-limiting example takes the form of a method of vision therapy, comprising: performing phosphene testing on a patient to determine one or more right eye phosphene thresholds for the patient (such as using FIGS. 4A-4I and the right eye); performing phosphene testing on a patient to determine one or more left eye phosphene thresholds for the patient (such as repeating FIGS. 4A-4I with the left eye). The method can next include issuing therapy to the patient by simultaneously generating therapy stimuli to the right and left eyes of the patient, wherein the therapy stimuli issued to the right eye are set according to the right eye phosphene thresholds, and the therapy stimuli issued to the left eye are set according to the left eye phosphene thresholds. This may be performed as illustrated at FIG. 4I, noting that the left and right eyes have different inputs/parameters in the Figure (note differences in impedance). The sliders in FIG. 4I are shown using scaled outputs; the actual amplitudes may be very different on left and right sides, depending on the results of the phosphene threshold testing.

Additionally or alternatively, the steps of performing phosphene testing are each performed to generate and store the following thresholds: a right eye full-field phosphene threshold; a right eye partial-field phosphene threshold; a left eye full-field phosphene threshold; and a left eye partial-field phosphene threshold, using, again, the methods of FIGS. 4A-4I.

Additionally or alternatively, the step of issuing therapy to the patient is generated as follows: therapy stimuli issued to the right eye have an amplitude between the right eye full-field phosphene threshold and the right eye partial-field phosphene threshold; and therapy stimuli issued to the left eye have an amplitude between the left eye full-field phosphene threshold and the left eye partial-field phosphene threshold. Again this can be understood form FIG. 4I.

Additionally or alternatively, the step of issuing therapy to the patient is generated as follows: therapy stimuli issued to the right eye have a first amplitude below the right eye partial-field phosphene threshold; and therapy stimuli issued to the left eye have a second amplitude below the left eye partial-field phosphene threshold. Again this can be understood form FIG. 4I, noting that the sliders may indicate amplitudes at or below the partial field thresholds for either or both eyes. It should also be noted that the therapy style may vary between the eyes, for example, sub-partial field threshold therapy may be used on one eye, and the other eye may receive no therapy, therapy using sub-partial field threshold therapy, therapy using amplitudes between the partial field threshold and full field threshold, or therapy above the full-field threshold. Other combinations can be used. There may be various reasons to use different combinations; for example, only causing phosphenes in one eye may be useful tot allow the patient to remain ambulatory during therapy. Or a patient may have one eye which is more greatly affected by a disease state or otherwise in need of more therapy.

Additionally or alternatively, issuing therapy includes: issuing therapy to the right eye at the first amplitude; raising an amplitude of therapy issued to the right eye above the right eye partial-field phosphene threshold; receiving an input indicating the patient observed phosphenes in the right eye; and returning to issuing therapy to the right eye at the first amplitude. Additionally or alternatively, issuing therapy includes: issuing therapy to the left eye at the second amplitude; raising an amplitude of therapy issued to the left eye above the left eye partial-field phosphene threshold; receiving an input indicating the patient observed phosphenes in the left eye; and returning to issuing therapy to the left eye at the second amplitude. These approaches to patient-driven or controlled phosphene threshold testing/confirmation has been described previously with the patient pushing and holding an icon or button until phosphenes are identified, or pushing the icon/button once to start the therapy ramp, and again to indicate the phosphenes were seen.

Additionally or alternatively, the method may include determining a test amplitude at which the patient observed phosphenes in the right eye; comparing the test amplitude to the right eye partial-field phosphene threshold; and: if the test amplitude is greater than the right eye partial-field phosphene threshold, adjusting the right eye partial-field phosphene threshold up and storing an adjusted right eye partial field phosphene threshold; if the test amplitude is less than the right eye partial-field phosphene threshold, adjusting the right eye partial-field phosphene threshold down and storing an adjusted right eye partial field phosphene threshold; or if the test amplitude is the same as the right eye partial-field phosphene threshold, preserving the stored right eye partial field phosphene threshold. Here, the newly acquired information during a therapy regimen can be used to update a stored threshold. Updating may include simply replacing the old threshold with the newly calculated one. Updating may instead include using a smoothing function, such as by averaging the new, test amplitude with the previously stored partial field threshold to generate the updated partial field phosphene threshold. The process can be performed instead or in addition using the full-field phosphene threshold.

Still another example takes the form of a therapy delivery apparatus for provision vision therapy, the apparatus comprising: a wearable eyepiece shaped to be held near and/or surround the eyes of a patient; an upper right electrode positioned on the wearable eyepiece to be located on the forehead of the patient above the patient's right eye when the wearable eyepiece is worn; an upper left electrode positioned on the wearable eyepiece to be located on the forehead of the patient above the patient's left eye when the wearable eyepiece is worn; a lower right electrode positioned on the wearable eyepiece to be located on face of the patient below the patient's right eye when the wearable eyepiece is worn; and a lower left electrode positioned on the wearable eyepiece to be located on face of the patient below the patient's right eye when the wearable eyepiece is worn. FIGS. 1-2 show such an eyepiece.

Additionally or alternatively, the apparatus may also include a pulse generator coupled to the upper right electrode, the lower right electrode, the upper left electrode, and the lower left electrode, the pulse generator having therein a power source, therapy output circuitry, sensing circuitry, and a user interface, the user interface allowing a user to turn the pulse generator on and/or off. FIGS. 7A-7B show such a pulse generator.

Additionally or alternatively, the user interface further allows the user to: modify therapy programs; perform phosphene threshold testing; and observe patient compliance with therapeutic goals. Such user interfaces are shown in FIGS. 3A-3B (modify therapy programs), 4A-4I (perform phosphene threshold testing) and 6 (observe compliance).

Additionally or alternatively, the pulse generator includes a communication circuit, and the therapy delivery apparatus includes a programmer configured to communicate with the communication circuit of the pulse generator; FIGS. 7A-7B show such a pulse generator, and FIG. 5 shows a mobile device as a programmer. Further, the programmer may include a user interface configured to allow a user to: modify therapy programs; perform phosphene threshold testing; and observe patient compliance with therapeutic goals. Such user interfaces are shown in FIGS. 3A-3B (modify therapy programs), 4A-4I (perform phosphene threshold testing) and 6 (observe compliance).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A method of vision therapy comprising:
presenting, on a user interface, an option to select a phosphene test to perform;
receiving a selection of the phosphene test;
presenting, on a user interface, an option to select the right eye or the left eye as a first eye for testing;
executing the phosphene test on the first eye by:
delivering an output stimulus to the region of the first eye starting at a first amplitude, and increasing the amplitude of the output stimulus;
receiving a first indication of partial field phosphenes being observed by the patient;
storing a second amplitude upon receipt of the first indication as a partial phosphene threshold; and
continuing to increase the amplitude of the output stimulus until at least one of:
identifying a stop condition; or
receiving a second indication of full field phosphenes being observed by the patient.

2. The method of vision therapy of claim 1, wherein the continuing to increase step is performed until receiving the second indication, and the method further comprises storing a third amplitude upon receipt of the second indication.

3. The method of vision therapy of claim 2, further comprising delivering a therapeutic output stimulus to the first eye having an amplitude between the second amplitude and the third amplitude.

4. The method of vision therapy of claim 2, further comprising:

delivering a therapeutic output stimulus to the first eye having an amplitude below the second amplitude;

receiving an input from the patient requesting to confirm therapy;

increasing the amplitude of the therapeutic stimulus above the second amplitude;

receiving an input from the patient confirming occurrence of phosphenes while the amplitude is increased above the second amplitude; and returning to delivering the therapeutic output stimulus having an amplitude below the second amplitude.

5. The method of claim 1, further comprising, after executing the phosphene test on the first eye, executing the phosphene test on a second eye of the patient by:

delivering an output stimulus to the region of the second eye of the patient starting at the first amplitude, and increasing the amplitude of the output stimulus;

receiving a third indication of partial field phosphenes being observed by the patient;

storing a fourth amplitude upon receipt of the third indication as a partial phosphene threshold; and again continuing to increase the amplitude of the output stimulus until at least one of:

identifying a stop condition; or receiving a fourth indication of full field phosphenes being observed by the patient.

6. The method of vision therapy of claim 5, wherein the again continuing to increase step is performed until receiving the fourth indication, and the method further comprises storing a fifth amplitude upon receipt of the second indication.

7. The method of vision therapy of claim 6, further comprising delivering a therapeutic output stimulus using a therapy delivery apparatus having an upper right electrode, a lower right electrode, an upper left electrode, and a lower left electrode, the therapy delivery apparatus being wearable on the face of the patient such that the upper right electrode is located above the right eye, the lower right electrode is located below the right eye, the upper left electrode is located above the left eye, and the lower left electrode is located below the left eye, by issuing a first therapeutic output stimulus having an amplitude between the second amplitude and the third amplitude and issuing a second therapeutic stimulus having an amplitude between the fourth amplitude and the fifth amplitude as follows:

if the first eye is the patient's right eye, issuing the first therapeutic stimulus using the upper right electrode and lower right electrode and issuing the second therapeutic stimulus using the upper left electrode and the lower left electrode; and if the first eye is the patient's left eye, issuing the first therapeutic stimulus using the upper left electrode and lower left electrode and issuing the second therapeutic stimulus using the upper right electrode and the lower right electrode.

8. The method of claim 1, wherein the output stimulus is generated by a pulse generator, and the user interface is part of the pulse generator.

9. The method of claim 1, wherein the output stimulus is generated by a pulse generator, and the user interface is part of a programmer, the programmer being in communication with the pulse generator.

* * * * *